(12) United States Patent
Sloan et al.

(10) Patent No.: US 7,766,829 B2
(45) Date of Patent: Aug. 3, 2010

(54) METHOD AND SYSTEM FOR PROVIDING BASAL PROFILE MODIFICATION IN ANALYTE MONITORING AND MANAGEMENT SYSTEMS

(75) Inventors: Mark K. Sloan, Hayward, CA (US); Gary Hayter, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 588 days.

(21) Appl. No.: 11/267,724

(22) Filed: Nov. 4, 2005

(65) Prior Publication Data

US 2007/0106135 A1    May 10, 2007

(51) Int. Cl.
*A61B 5/00* (2006.01)
*A61B 5/05* (2006.01)
*A61N 1/30* (2006.01)

(52) U.S. Cl. .................. 600/309; 600/347; 600/365; 604/19

(58) Field of Classification Search ............... 600/347, 600/365
See application file for complete search history.

(56) References Cited

U.S. PATENT DOCUMENTS

| | | | |
|---|---|---|---|
| 3,260,656 A | 7/1966 | Ross, Jr. | |
| 3,304,413 A | 2/1967 | Lehmann et al. | |
| 3,581,062 A | 5/1971 | Aston | |
| 3,651,318 A | 3/1972 | Czekajewski | |
| 3,653,841 A | 4/1972 | Klein | |
| 3,698,386 A | 10/1972 | Fried | |
| 3,719,564 A | 3/1973 | Lilly, Jr. et al. | |
| 3,768,014 A | 10/1973 | Smith et al. | |
| 3,776,832 A | 12/1973 | Oswin et al. | |
| 3,837,339 A | 9/1974 | Aisenberg et al. | |
| 3,919,051 A | 11/1975 | Koch et al. | |
| 3,926,760 A | 12/1975 | Allen et al. | |
| 3,949,388 A | 4/1976 | Fuller | |
| 3,972,320 A | 8/1976 | Kalman | |
| 3,979,274 A | 9/1976 | Newman | |
| 4,008,717 A | 2/1977 | Kowarski | |
| 4,016,866 A | 4/1977 | Lawton | |
| 4,036,749 A | 7/1977 | Anderson | |
| 4,055,175 A * | 10/1977 | Clemens et al. ............... 604/66 |

(Continued)

FOREIGN PATENT DOCUMENTS

DE    4234553    1/1995

(Continued)

OTHER PUBLICATIONS

International Search Report & Written Opinion of the International Searching Authority, for PCT Application No. PCT/US2006/060394 filed Oct. 31, 2006.
International Preliminary Report on Patentability and Written Opinion of the International Searching Authority for PCT Application No. PCT/US2006/060394 filed Oct. 31, 2006 to Abbott Diabetes Care, Inc., et al. mailed May 15, 2008.

(Continued)

*Primary Examiner*—Patricia C Mallari
(74) *Attorney, Agent, or Firm*—Jackson & Co., LLP

(57) ABSTRACT

Method and system for providing basal profile modification in insulin therapy for use with infusion devices includes periodically monitoring the analyte levels of a patient for a predetermined period of time in order to determine, based on the monitored analyte levels, an appropriate modification factor to be incorporated into the underlying basal profile which was running at the time the periodic monitoring of the analyte levels were performed.

26 Claims, 4 Drawing Sheets

U.S. PATENT DOCUMENTS

| | | |
|---|---|---|
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,129,128 A | 12/1978 | McFarlane |
| 4,151,845 A | 5/1979 | Clemens |
| 4,154,231 A | 5/1979 | Russell |
| 4,168,205 A | 9/1979 | Danninger et al. |
| 4,172,770 A | 10/1979 | Semersky et al. |
| 4,178,916 A | 12/1979 | McNamara |
| 4,206,755 A | 6/1980 | Klein |
| 4,224,125 A | 9/1980 | Nakamura et al. |
| 4,240,438 A | 12/1980 | Updike et al. |
| 4,240,889 A | 12/1980 | Yoda et al. |
| 4,245,634 A | 1/1981 | Albisser et al. |
| 4,247,297 A | 1/1981 | Berti et al. |
| 4,271,449 A | 6/1981 | Grogan |
| 4,318,784 A | 3/1982 | Higgins et al. |
| 4,327,725 A | 5/1982 | Cortese et al. |
| 4,331,869 A | 5/1982 | Rollo |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,356,074 A | 10/1982 | Johnson |
| 4,365,637 A | 12/1982 | Johnson |
| 4,366,033 A | 12/1982 | Richter et al. |
| 4,375,399 A | 3/1983 | Havas et al. |
| 4,384,586 A | 5/1983 | Christiansen |
| 4,390,621 A | 6/1983 | Bauer |
| 4,392,933 A | 7/1983 | Nakamura et al. |
| 4,401,122 A | 8/1983 | Clark, Jr. |
| 4,404,066 A | 9/1983 | Johnson |
| 4,407,959 A | 10/1983 | Tsuji et al. |
| 4,417,588 A | 11/1983 | Houghton et al. |
| 4,418,148 A | 11/1983 | Oberhardt |
| 4,420,564 A | 12/1983 | Tsuji et al. |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,444,892 A | 4/1984 | Malmros |
| 4,450,842 A | 5/1984 | Zick et al. |
| 4,458,686 A | 7/1984 | Clark, Jr. |
| 4,461,691 A | 7/1984 | Frank |
| 4,467,811 A | 8/1984 | Clark, Jr. |
| 4,469,110 A | 9/1984 | Slama |
| 4,477,314 A | 10/1984 | Richter et al. |
| 4,478,976 A | 10/1984 | Goertz et al. |
| 4,483,924 A | 11/1984 | Tsuji et al. |
| 4,484,987 A | 11/1984 | Gough |
| 4,494,950 A | 1/1985 | Fischell |
| 4,509,531 A | 4/1985 | Ward |
| 4,512,348 A | 4/1985 | Uchigaki et al. |
| 4,522,690 A | 6/1985 | Venkatsetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,569,589 A | 2/1986 | Neufeld |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,595,479 A | 6/1986 | Kimura et al. |
| 4,619,754 A | 10/1986 | Niki et al. |
| 4,619,793 A | 10/1986 | Lee |
| 4,627,445 A | 12/1986 | Garcia et al. |
| 4,627,908 A | 12/1986 | Miller |
| 4,633,878 A | 1/1987 | Bombardien |
| 4,633,881 A | 1/1987 | Moore et al. |
| 4,637,403 A | 1/1987 | Garcia et al. |
| 4,648,408 A | 3/1987 | Hutcheson et al. |
| 4,650,547 A | 3/1987 | Gough |
| 4,653,513 A | 3/1987 | Dombrowski |
| 4,654,197 A | 3/1987 | Lilja et al. |
| 4,655,880 A | 4/1987 | Liu |
| 4,655,885 A | 4/1987 | Hill et al. |
| 4,658,463 A | 4/1987 | Sugita et al. |
| 4,671,288 A | 6/1987 | Gough |
| 4,674,652 A | 6/1987 | Aten et al. |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,686,624 A | 8/1987 | Blum et al. |
| 4,703,756 A | 11/1987 | Gough et al. |
| 4,711,245 A | 12/1987 | Higgins et al. |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,731,726 A | 3/1988 | Allen, III |
| 4,749,985 A | 6/1988 | Corsberg |
| 4,750,496 A | 6/1988 | Reinhart |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,803,625 A | 2/1989 | Fu et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| 4,835,372 A | 5/1989 | Gombrich et al. |
| RE32,947 E | 6/1989 | Dormer et al. |
| 4,837,049 A | 6/1989 | Byers et al. |
| 4,840,893 A | 6/1989 | Hill et al. |
| RE32,974 E | 7/1989 | Porat et al. |
| 4,844,076 A | 7/1989 | Lesho et al. |
| 4,845,035 A | 7/1989 | Fanta et al. |
| 4,848,351 A | 7/1989 | Finch |
| 4,854,322 A | 8/1989 | Ash et al. |
| 4,856,340 A | 8/1989 | Garrison |
| 4,857,713 A | 8/1989 | Brown |
| 4,858,617 A | 8/1989 | Sanders |
| 4,870,561 A | 9/1989 | Love et al. |
| 4,871,351 A | 10/1989 | Feingold |
| 4,871,440 A | 10/1989 | Nagata et al. |
| 4,874,499 A | 10/1989 | Smith et al. |
| 4,874,500 A | 10/1989 | Madou et al. |
| 4,890,620 A | 1/1990 | Gough |
| 4,890,621 A | 1/1990 | Hakky |
| 4,894,137 A | 1/1990 | Takizawa et al. |

| Patent No. | Date | Inventor |
|---|---|---|
| 4,897,162 A | 1/1990 | Lewandowski et al. |
| 4,897,173 A | 1/1990 | Nankai et al. |
| 4,899,839 A | 2/1990 | Dessertine et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,920,969 A | 5/1990 | Suzuki |
| 4,920,977 A | 5/1990 | Haynes |
| 4,923,586 A | 5/1990 | Katayama et al. |
| 4,925,268 A | 5/1990 | Iyer et al. |
| 4,927,516 A | 5/1990 | Yamaguchi et al. |
| 4,931,795 A | 6/1990 | Gord |
| 4,934,369 A | 6/1990 | Maxwell |
| 4,935,105 A | 6/1990 | Churchouse |
| 4,935,345 A | 6/1990 | Guibeau et al. |
| 4,936,956 A | 6/1990 | Wrighton |
| 4,938,860 A | 7/1990 | Wogoman |
| 4,942,127 A | 7/1990 | Wada et al. |
| 4,944,299 A | 7/1990 | Silvian |
| 4,945,045 A | 7/1990 | Forrest et al. |
| 4,950,378 A | 8/1990 | Nagata |
| 4,953,552 A | 9/1990 | DeMarzo |
| 4,954,129 A | 9/1990 | Giuliani et al. |
| 4,957,115 A | 9/1990 | Selker |
| 4,958,632 A | 9/1990 | Duggan |
| 4,968,400 A | 11/1990 | Shimomura et al. |
| 4,969,468 A | 11/1990 | Byers et al. |
| 4,970,145 A | 11/1990 | Bennetto et al. |
| 4,974,929 A | 12/1990 | Curry |
| 4,979,509 A | 12/1990 | Hakky |
| 4,986,271 A | 1/1991 | Wilkins |
| 4,990,845 A | 2/1991 | Gord |
| 4,991,582 A | 2/1991 | Byers et al. |
| 4,994,068 A | 2/1991 | Hufnagie |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,002,054 A | 3/1991 | Ash et al. |
| 5,007,427 A | 4/1991 | Suzuki et al. |
| 5,016,172 A | 5/1991 | Dessertine |
| 5,016,201 A | 5/1991 | Bryan et al. |
| 5,019,974 A | 5/1991 | Beckers |
| 5,034,192 A | 7/1991 | Wrighton et al. |
| 5,035,860 A | 7/1991 | Kleingeld et al. |
| 5,036,860 A | 8/1991 | Leigh et al. |
| 5,036,861 A | 8/1991 | Sembrowich et al. |
| 5,037,527 A | 8/1991 | Hayashi et al. |
| 5,049,487 A | 9/1991 | Phillips et al. |
| 5,050,612 A | 9/1991 | Matsumura |
| 5,055,171 A | 10/1991 | Peck |
| 5,058,592 A | 10/1991 | Whisler |
| 5,063,081 A | 11/1991 | Cozzette et al. |
| 5,068,536 A | 11/1991 | Rosenthal |
| 5,070,535 A | 12/1991 | Hochmair et al. |
| 5,073,500 A | 12/1991 | Saito et al. |
| 5,077,476 A | 12/1991 | Rosenthal |
| 5,078,854 A | 1/1992 | Burgess et al. |
| 5,082,550 A | 1/1992 | Rishpon et al. |
| 5,082,786 A | 1/1992 | Nakamoto |
| 5,084,828 A | 1/1992 | Kaufman et al. |
| 5,089,112 A | 2/1992 | Skotheim et al. |
| 5,094,951 A | 3/1992 | Rosenberg |
| 5,095,904 A | 3/1992 | Seligman et al. |
| 5,096,560 A | 3/1992 | Takai et al. |
| 5,096,836 A | 3/1992 | Macho et al. |
| 5,101,814 A | 4/1992 | Palti |
| 5,104,814 A | 4/1992 | Chipkin et al. |
| 5,106,365 A | 4/1992 | Hernandez |
| 5,108,564 A | 4/1992 | Szuminsky et al. |
| 5,109,850 A | 5/1992 | Blanco et al. |
| 5,111,539 A | 5/1992 | Hiruta et al. |
| 5,111,818 A | 5/1992 | Suzuki et al. |
| 5,114,678 A | 5/1992 | Crawford et al. |
| 5,120,420 A | 6/1992 | Nankai et al. |
| 5,120,421 A | 6/1992 | Glass et al. |
| 5,122,925 A | 6/1992 | Inpyn |
| 5,126,034 A | 6/1992 | Carter et al. |
| 5,126,247 A | 6/1992 | Palmer et al. |
| 5,130,009 A | 7/1992 | Marsoner et al. |
| 5,133,856 A | 7/1992 | Yamaguchi et al. |
| 5,134,391 A | 7/1992 | Okada |
| 5,135,003 A | 8/1992 | Souma |
| 5,139,023 A | 8/1992 | Stanley et al. |
| 5,140,393 A | 8/1992 | Hijikihigawa et al. |
| 5,141,868 A | 8/1992 | Shanks et al. |
| 5,161,532 A | 11/1992 | Joseph |
| 5,165,407 A | 11/1992 | Wilson et al. |
| 5,168,046 A | 12/1992 | Hamamoto et al. |
| 5,174,291 A | 12/1992 | Schoonen et al. |
| 5,176,644 A | 1/1993 | Srisathapat et al. |
| 5,176,662 A | 1/1993 | Bartholomew et al. |
| 5,182,707 A | 1/1993 | Cooper et al. |
| 5,184,359 A | 2/1993 | Tsukamura et al. |
| 5,185,256 A | 2/1993 | Nankai et al. |
| 5,190,041 A | 3/1993 | Palti |
| 5,192,415 A | 3/1993 | Yoshioka et al. |
| 5,192,416 A | 3/1993 | Wang et al. |
| 5,193,539 A | 3/1993 | Schulman et al. |
| 5,193,540 A | 3/1993 | Schulman et al. |
| 5,197,322 A | 3/1993 | Indravudh |
| 5,198,367 A | 3/1993 | Aizawa et al. |
| 5,200,051 A | 4/1993 | Cozzette et al. |
| 5,202,261 A | 4/1993 | Musho et al. |
| 5,205,920 A | 4/1993 | Oyama et al. |
| 5,206,145 A | 4/1993 | Cattell |
| 5,208,154 A | 5/1993 | Weaver et al. |
| 5,209,229 A | 5/1993 | Gilli |
| 5,215,887 A | 6/1993 | Saito |
| 5,216,597 A | 6/1993 | Beckers |
| 5,217,442 A | 6/1993 | Davis |
| 5,217,595 A | 6/1993 | Smith et al. |
| 5,227,042 A | 7/1993 | Zawodzinski et al. |
| 5,229,282 A | 7/1993 | Yoshioka et al. |
| 5,246,867 A | 9/1993 | Lakowicz et al. |
| 5,250,439 A | 10/1993 | Musho et al. |
| 5,251,126 A * | 10/1993 | Kahn et al. .................. 600/309 |
| 5,257,971 A | 11/1993 | Lord et al. |
| 5,257,980 A | 11/1993 | Van Antwerp et al. |
| 5,261,401 A | 11/1993 | Baker et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,265,888 A | 11/1993 | Yamamoto et al. |
| 5,266,179 A | 11/1993 | Nankai et al. |
| 5,269,212 A | 12/1993 | Peters et al. |
| 5,271,815 A | 12/1993 | Wong |
| 5,272,060 A | 12/1993 | Hamamoto et al. |
| 5,275,159 A | 1/1994 | Griebel |
| 5,278,079 A | 1/1994 | Gubinski et al. |
| 5,279,294 A | 1/1994 | Anderson |
| 5,282,950 A | 2/1994 | Dietze et al. |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,291,887 A | 3/1994 | Stanley et al. |
| 5,293,546 A | 3/1994 | Tadros et al. |
| 5,293,877 A | 3/1994 | O'Hara et al. |
| 5,299,571 A | 4/1994 | Mastrototaro |

| | | | | | |
|---|---|---|---|---|---|
| 5,304,468 A | 4/1994 | Phillips et al. | 5,505,709 A | 4/1996 | Funderburk |
| 5,307,263 A | 4/1994 | Brown | 5,505,713 A | 4/1996 | Van Antwerp et al. |
| 5,309,919 A | 5/1994 | Snell et al. | 5,507,288 A | 4/1996 | Bocker et al. |
| 5,310,885 A | 5/1994 | Maier et al. | 5,508,171 A | 4/1996 | Walling et al. |
| 5,320,098 A | 6/1994 | Davidson | 5,509,410 A | 4/1996 | Hill et al. |
| 5,320,725 A | 6/1994 | Gregg et al. | 5,514,103 A | 5/1996 | Srisathapat et al. |
| 5,322,063 A | 6/1994 | Allen et al. | 5,514,253 A | 5/1996 | Davis et al. |
| 5,324,303 A | 6/1994 | Strong et al. | 5,514,718 A | 5/1996 | Lewis et al. |
| 5,324,316 A | 6/1994 | Schulman et al. | 5,518,006 A | 5/1996 | Mawhirt et al. |
| 5,326,449 A | 7/1994 | Cunningham | 5,520,787 A | 5/1996 | Hanagan et al. |
| 5,337,258 A | 8/1994 | Dennis | 5,522,865 A | 6/1996 | Schulman et al. |
| 5,337,747 A | 8/1994 | Neftei | 5,525,511 A | 6/1996 | D'Costa |
| 5,340,722 A | 8/1994 | Wolfbeis et al. | 5,526,120 A | 6/1996 | Jina et al. |
| 5,342,789 A | 8/1994 | Chick et al. | 5,527,307 A | 6/1996 | Srisathapat et al. |
| 5,352,348 A | 10/1994 | Young et al. | 5,529,676 A | 6/1996 | Maley et al. |
| 5,356,348 A | 10/1994 | Bellio et al. | 5,531,878 A | 7/1996 | Vadgama et al. |
| 5,356,786 A | 10/1994 | Heller et al. | 5,538,511 A | 7/1996 | Van Antwerp et al. |
| 5,358,514 A | 10/1994 | Schulman et al. | 5,545,152 A | 8/1996 | Funderburk et al. |
| 5,360,404 A | 11/1994 | Novacek et al. | 5,545,191 A | 8/1996 | Mann et al. |
| 5,364,797 A | 11/1994 | Olson et al. | 5,549,113 A | 8/1996 | Halleck et al. |
| 5,366,609 A | 11/1994 | White et al. | 5,549,115 A | 8/1996 | Morgan et al. |
| 5,368,028 A | 11/1994 | Palti | 5,552,027 A | 9/1996 | Birkle et al. |
| 5,370,622 A | 12/1994 | Livingston et al. | 5,554,166 A | 9/1996 | Lange et al. |
| 5,371,687 A | 12/1994 | Holmes, II et al. | 5,556,524 A | 9/1996 | Albers |
| 5,372,133 A | 12/1994 | Hogen Esch | 5,560,357 A | 10/1996 | Faupel et al. |
| 5,372,427 A | 12/1994 | Padovani et al. | 5,562,713 A | 10/1996 | Silvian |
| 5,376,070 A | 12/1994 | Purvis et al. | 5,565,085 A | 10/1996 | Ikeda et al. |
| 5,376,251 A | 12/1994 | Kaneko et al. | 5,567,302 A | 10/1996 | Song et al. |
| 5,377,258 A | 12/1994 | Bro | 5,568,806 A | 10/1996 | Cheney, II et al. |
| 5,378,628 A | 1/1995 | Gratzel et al. | 5,569,186 A | 10/1996 | Lord et al. |
| 5,379,238 A | 1/1995 | Stark | 5,569,212 A | 10/1996 | Brown |
| 5,380,422 A | 1/1995 | Negishi et al. | 5,573,647 A | 11/1996 | Maley et al. |
| 5,382,346 A | 1/1995 | Uenoyama et al. | 5,575,895 A | 11/1996 | Ikeda et al. |
| 5,387,327 A | 2/1995 | Khan | 5,580,527 A | 12/1996 | Bell et al. |
| 5,390,671 A | 2/1995 | Lord et al. | 5,580,794 A | 12/1996 | Allen |
| 5,391,250 A | 2/1995 | Cheney, II et al. | 5,582,184 A | 12/1996 | Erickson et al. |
| 5,393,903 A | 2/1995 | Gratzel et al. | 5,582,697 A | 12/1996 | Ikeda et al. |
| 5,395,504 A | 3/1995 | Saurer et al. | 5,582,698 A | 12/1996 | Flaherty et al. |
| 5,399,823 A | 3/1995 | McCusker | 5,584,813 A | 12/1996 | Livingston et al. |
| 5,400,782 A | 3/1995 | Beaubiah | 5,586,553 A | 12/1996 | Halli et al. |
| 5,408,999 A | 4/1995 | Singh et al. | 5,589,326 A | 12/1996 | Deng et al. |
| 5,410,471 A | 4/1995 | Alyfuku et al. | 5,593,852 A | 1/1997 | Heller et al. |
| 5,410,474 A | 4/1995 | Fox | 5,594,906 A | 1/1997 | Holmes, II et al. |
| 5,411,647 A | 5/1995 | Johnson et al. | 5,596,150 A | 1/1997 | Arndt et al. |
| 5,413,690 A | 5/1995 | Kost et al. | 5,596,994 A | 1/1997 | Bro |
| 5,422,246 A | 6/1995 | Koopal et al. | 5,601,435 A | 2/1997 | Quy |
| 5,431,160 A | 7/1995 | Wilkins | 5,601,694 A | 2/1997 | Maley et al. |
| 5,431,691 A | 7/1995 | Snell et al. | 5,605,152 A | 2/1997 | Slate et al. |
| 5,431,921 A | 7/1995 | Thombre | 5,609,575 A * | 3/1997 | Larson et al. .................. 604/65 |
| 5,433,710 A | 7/1995 | Van Antwerp et al. | 5,611,900 A | 3/1997 | Worden et al. |
| 5,437,973 A | 8/1995 | Vadgama et al. | 5,615,671 A | 4/1997 | Schoonen et al. |
| 5,437,999 A | 8/1995 | Diebold et al. | 5,616,222 A | 4/1997 | Maley et al. |
| 5,445,611 A | 8/1995 | Eppstein et al. | 5,617,851 A | 4/1997 | Lipkovker |
| 5,445,920 A | 8/1995 | Saito | 5,623,925 A | 4/1997 | Swenson et al. |
| 5,456,692 A | 10/1995 | Smith, Jr. et al. | 5,628,309 A | 5/1997 | Brown |
| 5,456,940 A | 10/1995 | Funderburk | 5,628,310 A | 5/1997 | Rao et al. |
| 5,458,140 A | 10/1995 | Eppstein et al. | 5,628,890 A | 5/1997 | Carter et al. |
| 5,460,618 A | 10/1995 | Harreld | 5,629,981 A | 5/1997 | Nerlikar |
| 5,462,525 A | 10/1995 | Srisathapat et al. | 5,637,095 A | 6/1997 | Nason et al. |
| 5,462,645 A | 10/1995 | Albery et al. | 5,640,764 A | 6/1997 | Strojnik |
| 5,466,218 A | 11/1995 | Srisathapat et al. | 5,640,954 A | 6/1997 | Pfeiffer et al. |
| 5,469,846 A | 11/1995 | Khan | 5,643,212 A | 7/1997 | Coutre et al. |
| 5,472,317 A | 12/1995 | Field et al. | 5,647,853 A | 7/1997 | Feldmann et al. |
| 5,476,460 A | 12/1995 | Montalvo | 5,650,062 A | 7/1997 | Ikeda et al. |
| 5,477,855 A | 12/1995 | Schindler et al. | 5,651,767 A | 7/1997 | Schulman et al. |
| 5,482,473 A | 1/1996 | Lord et al. | 5,651,869 A | 7/1997 | Yoshioka et al. |
| 5,484,404 A | 1/1996 | Schulman et al. | 5,653,239 A | 8/1997 | Pompei et al. |
| 5,487,751 A | 1/1996 | Radons et al. | 5,660,163 A | 8/1997 | Schulman et al. |
| 5,491,474 A | 2/1996 | Suni et al. | 5,665,065 A | 9/1997 | Colman et al. |
| 5,494,562 A | 2/1996 | Maley et al. | 5,665,222 A | 9/1997 | Heller et al. |
| 5,496,453 A | 3/1996 | Uenoyama et al. | 5,667,983 A | 9/1997 | Abel et al. |
| 5,497,772 A | 3/1996 | Schulman et al. | 5,670,031 A | 9/1997 | Hintsche et al. |
| 5,501,956 A | 3/1996 | Wada et al. | 5,678,571 A | 10/1997 | Brown |

| | | | | | |
|---|---|---|---|---|---|
| 5,679,690 A | 10/1997 | Andre et al. | 5,872,713 A | 2/1999 | Douglas et al. |
| 5,680,858 A | 10/1997 | Hansen et al. | 5,876,484 A | 3/1999 | Raskin et al. |
| 5,682,233 A | 10/1997 | Brinda | 5,879,163 A | 3/1999 | Brown et al. |
| 5,686,717 A | 11/1997 | Knowles et al. | 5,879,311 A | 3/1999 | Duchon et al. |
| 5,695,623 A | 12/1997 | Michel et al. | 5,880,829 A | 3/1999 | Kauhaniemi et al. |
| 5,695,949 A | 12/1997 | Galen et al. | 5,882,494 A | 3/1999 | Van Antwerp |
| 5,701,894 A | 12/1997 | Cherry et al. | 5,885,211 A | 3/1999 | Eppstein et al. |
| 5,704,922 A | 1/1998 | Brown | 5,887,133 A | 3/1999 | Brown et al. |
| 5,707,502 A | 1/1998 | McCaffrey et al. | 5,897,493 A | 4/1999 | Brown |
| 5,708,247 A | 1/1998 | McAleer et al. | 5,898,025 A | 4/1999 | Burg et al. |
| 5,710,630 A | 1/1998 | Essenpreis et al. | 5,899,855 A | 5/1999 | Brown |
| 5,711,001 A | 1/1998 | Bussan et al. | 5,913,310 A | 6/1999 | Brown |
| 5,711,297 A | 1/1998 | Iliff et al. | 5,917,346 A | 6/1999 | Gord |
| 5,711,861 A | 1/1998 | Ward et al. | 5,918,603 A | 7/1999 | Brown |
| 5,711,862 A | 1/1998 | Sakoda et al. | 5,925,021 A | 7/1999 | Castellano et al. |
| 5,711,868 A | 1/1998 | Maley et al. | 5,931,791 A | 8/1999 | Saltzstein et al. |
| 5,718,234 A | 2/1998 | Warden et al. | 5,933,136 A | 8/1999 | Brown |
| 5,720,733 A | 2/1998 | Brown | 5,940,801 A | 8/1999 | Brown |
| 5,720,862 A | 2/1998 | Hamamoto et al. | 5,942,979 A | 8/1999 | Luppino |
| 5,721,783 A | 2/1998 | Anderson | 5,945,345 A | 8/1999 | Blatt et al. |
| 5,722,397 A | 3/1998 | Eppstein | 5,947,921 A | 9/1999 | Johnson et al. |
| 5,727,548 A | 3/1998 | Hill et al. | 5,948,512 A | 9/1999 | Kubota et al. |
| 5,730,124 A | 3/1998 | Yamauchi | 5,950,632 A | 9/1999 | Reber et al. |
| 5,730,654 A | 3/1998 | Brown | 5,951,300 A | 9/1999 | Brown |
| 5,735,273 A | 4/1998 | Kurnik et al. | 5,951,492 A | 9/1999 | Douglas et al. |
| 5,735,285 A | 4/1998 | Albert et al. | 5,951,521 A | 9/1999 | Mastrototaro et al. |
| 5,741,211 A | 4/1998 | Renirie et al. | 5,951,836 A | 9/1999 | McAleer et al. |
| 5,741,688 A | 4/1998 | Oxenboll et al. | 5,954,643 A | 9/1999 | Van Antwerp |
| 5,746,217 A | 5/1998 | Erickson et al. | 5,954,685 A | 9/1999 | Tierny |
| 5,750,926 A | 5/1998 | Schulman et al. | 5,954,700 A | 9/1999 | Kovelman |
| 5,770,028 A | 6/1998 | Maley et al. | 5,956,501 A | 9/1999 | Brown |
| 5,771,001 A | 6/1998 | Cobb | 5,957,854 A | 9/1999 | Besson et al. |
| 5,771,890 A | 6/1998 | Tamada | 5,957,890 A | 9/1999 | Mann et al. |
| 5,772,586 A | 6/1998 | Heinonen et al. | 5,957,958 A | 9/1999 | Schulman et al. |
| 5,777,060 A | 7/1998 | Van Antwerp | 5,960,403 A | 9/1999 | Brown |
| 5,779,665 A | 7/1998 | Mastrototaro et al. | 5,961,451 A | 10/1999 | Reber et al. |
| 5,782,814 A | 7/1998 | Brown et al. | 5,964,993 A | 10/1999 | Blubaugh, Jr. et al. |
| 5,785,681 A | 7/1998 | Indravudh | 5,965,380 A | 10/1999 | Heller et al. |
| 5,786,439 A | 7/1998 | Van Antwerp et al. | 5,968,839 A | 10/1999 | Blatt et al. |
| 5,786,584 A | 7/1998 | Button et al. | 5,971,922 A | 10/1999 | Arita et al. |
| 5,788,678 A | 8/1998 | Van Antwerp | 5,971,941 A | 10/1999 | Simons et al. |
| 5,791,344 A | 8/1998 | Schulman et al. | 5,974,124 A | 10/1999 | Schlueter, Jr. et al. |
| 5,792,117 A | 8/1998 | Brown | 5,977,476 A | 11/1999 | Guha et al. |
| 5,800,420 A | 9/1998 | Gross et al. | 5,981,294 A | 11/1999 | Blatt et al. |
| 5,804,048 A | 9/1998 | Wong et al. | 5,989,409 A | 11/1999 | Kurnik et al. |
| 5,807,315 A | 9/1998 | Van Antwerp et al. | 5,994,476 A | 11/1999 | Shin et al. |
| 5,807,375 A | 9/1998 | Gross et al. | 5,995,860 A | 11/1999 | Sun et al. |
| 5,814,599 A | 9/1998 | Mitragotri et al. | 5,997,476 A | 12/1999 | Brown |
| 5,820,551 A | 10/1998 | Hill et al. | 5,999,848 A | 12/1999 | Gord et al. |
| 5,820,570 A | 10/1998 | Erickson et al. | 5,999,849 A | 12/1999 | Gord et al. |
| 5,820,622 A | 10/1998 | Gross et al. | 6,001,067 A | 12/1999 | Shults et al. |
| 5,822,715 A | 10/1998 | Worthington et al. | 6,002,954 A | 12/1999 | Van Antwerp et al. |
| 5,825,488 A | 10/1998 | Kohl et al. | 6,002,961 A | 12/1999 | Mitragotri et al. |
| 5,827,179 A | 10/1998 | Lichter et al. | 6,004,441 A | 12/1999 | Fujiwara et al. |
| 5,827,183 A | 10/1998 | Kurnik et al. | 6,011,984 A | 1/2000 | Van Antwerp et al. |
| 5,827,184 A | 10/1998 | Netherly et al. | 6,014,577 A | 1/2000 | Henning et al. |
| 5,828,943 A | 10/1998 | Brown | 6,018,678 A | 1/2000 | Mitragotri et al. |
| 5,830,341 A | 11/1998 | Gilmartin | 6,023,629 A | 2/2000 | Tamada |
| 5,832,448 A | 11/1998 | Brown | 6,024,699 A | 2/2000 | Surwit et al. |
| 5,834,224 A | 11/1998 | Ruger et al. | 6,026,320 A | 2/2000 | Carlson et al. |
| 5,837,454 A | 11/1998 | Cozzette et al. | 6,027,459 A | 2/2000 | Shain et al. |
| 5,837,546 A | 11/1998 | Allen et al. | 6,027,692 A | 2/2000 | Galen et al. |
| 5,840,020 A | 11/1998 | Heinonen et al. | 6,032,059 A | 2/2000 | Henning et al. |
| 5,842,983 A | 12/1998 | Abel et al. | 6,032,199 A | 2/2000 | Lim et al. |
| 5,843,140 A | 12/1998 | Strojnik | 6,033,866 A | 3/2000 | Guo et al. |
| 5,846,702 A | 12/1998 | Deng et al. | 6,035,237 A | 3/2000 | Schulman et al. |
| 5,846,744 A | 12/1998 | Athey et al. | 6,040,194 A | 3/2000 | Chick et al. |
| 5,851,197 A | 12/1998 | Marano et al. | 6,041,253 A | 3/2000 | Kost et al. |
| 5,854,078 A | 12/1998 | Asher et al. | 6,043,437 A | 3/2000 | Schulman et al. |
| 5,854,189 A | 12/1998 | Kruse et al. | 6,049,727 A | 4/2000 | Crothall |
| 5,857,967 A | 1/1999 | Frid et al. | 6,056,718 A | 5/2000 | Funderburk et al. |
| 5,857,983 A | 1/1999 | Douglas et al. | 6,063,459 A | 5/2000 | Velte |
| 5,860,917 A | 1/1999 | Comanor et al. | 6,066,243 A | 5/2000 | Anderson et al. |

| | | | | | | | |
|---|---|---|---|---|---|---|---|
| 6,067,474 | A | 5/2000 | Schulman et al. | 6,239,925 | B1 | 5/2001 | Ardrey et al. |
| 6,068,615 | A | 5/2000 | Brown et al. | 6,241,862 | B1 | 6/2001 | McAleer et al. |
| 6,071,249 | A | 6/2000 | Cunningham et al. | 6,246,330 | B1 | 6/2001 | Nielsen |
| 6,071,251 | A | 6/2000 | Cunningham et al. | 6,246,992 | B1 | 6/2001 | Brown |
| 6,071,294 | A | 6/2000 | Simons et al. | 6,248,065 | B1 | 6/2001 | Brown |
| 6,071,391 | A | 6/2000 | Gotoh et al. | 6,248,067 | B1 | 6/2001 | Causey, III et al. |
| 6,081,736 | A | 6/2000 | Colvin et al. | 6,248,093 | B1 | 6/2001 | Moberg |
| 6,083,710 | A | 7/2000 | Heller et al. | 6,251,260 | B1 | 6/2001 | Heller et al. |
| 6,088,608 | A | 7/2000 | Schulman et al. | 6,252,032 | B1 | 6/2001 | Van Antwerp et al. |
| 6,091,975 | A | 7/2000 | Daddona et al. | 6,253,804 | B1 | 7/2001 | Safabash |
| 6,091,976 | A | 7/2000 | Pfeiffer et al. | 6,254,586 | B1 | 7/2001 | Mann et al. |
| 6,093,156 | A | 7/2000 | Cunningham et al. | 6,256,643 | B1 | 7/2001 | Cork et al. |
| 6,093,167 | A | 7/2000 | Houben et al. | 6,259,587 | B1 | 7/2001 | Sheldon et al. |
| 6,093,172 | A | 7/2000 | Funderburk et al. | 6,259,937 | B1 | 7/2001 | Schulman et al. |
| 6,097,831 | A | 8/2000 | Wieck et al. | 6,260,022 | B1 | 7/2001 | Brown |
| 6,099,484 | A | 8/2000 | Douglas et al. | 6,266,645 | B1 | 7/2001 | Simpson |
| 6,101,478 | A | 8/2000 | Brown | 6,267,724 | B1 | 7/2001 | Taylor |
| 6,103,033 | A | 8/2000 | Say et al. | 6,268,161 | B1 | 7/2001 | Han et al. |
| 6,106,780 | A | 8/2000 | Douglas et al. | 6,270,445 | B1 | 8/2001 | Dean, Jr. et al. |
| 6,110,148 | A | 8/2000 | Brown et al. | 6,272,364 | B1 | 8/2001 | Kurnik |
| 6,110,152 | A | 8/2000 | Kovelman | 6,275,717 | B1 | 8/2001 | Gross et al. |
| 6,113,578 | A | 9/2000 | Brown | 6,280,416 | B1 | 8/2001 | Van Antwerp et al. |
| 6,117,290 | A | 9/2000 | Say et al. | 6,280,587 | B1 | 8/2001 | Matsumoto |
| 6,119,028 | A | 9/2000 | Schulman et al. | 6,281,006 | B1 | 8/2001 | Heller et al. |
| 6,120,676 | A | 9/2000 | Heller et al. | 6,283,943 | B1 | 9/2001 | Dy et al. |
| 6,121,009 | A | 9/2000 | Heller et al. | 6,284,126 | B1 | 9/2001 | Kurnik et al. |
| 6,121,611 | A | 9/2000 | Lindsay et al. | 6,284,478 | B1 | 9/2001 | Heller et al. |
| 6,122,351 | A | 9/2000 | Schlueter, Jr. et al. | 6,293,925 | B1 | 9/2001 | Safabash et al. |
| 6,125,978 | A | 10/2000 | Ando et al. | 6,294,281 | B1 | 9/2001 | Heller |
| 6,134,461 | A | 10/2000 | Say et al. | 6,295,463 | B1 | 9/2001 | Stenzler |
| 6,134,504 | A | 10/2000 | Douglas et al. | 6,295,506 | B1 | 9/2001 | Heinonen et al. |
| 6,139,718 | A | 10/2000 | Kurnik et al. | 6,298,254 | B2 | 10/2001 | Tamada |
| 6,141,573 | A | 10/2000 | Kurnik et al. | 6,299,578 | B1 | 10/2001 | Kurnik et al. |
| 6,142,939 | A | 11/2000 | Eppstein et al. | 6,299,757 | B1 | 10/2001 | Feldman et al. |
| 6,143,164 | A | 11/2000 | Heller et al. | 6,301,499 | B1 | 10/2001 | Carlson et al. |
| 6,144,837 | A | 11/2000 | Quy | 6,304,766 | B1 | 10/2001 | Colvin, Jr. et al. |
| 6,144,869 | A | 11/2000 | Berner et al. | 6,306,104 | B1 | 10/2001 | Cunningham et al. |
| 6,144,922 | A | 11/2000 | Douglas et al. | 6,309,351 | B1 | 10/2001 | Kurnik et al. |
| 6,148,094 | A | 11/2000 | Kinsella | 6,309,884 | B1 | 10/2001 | Cooper et al. |
| 6,150,128 | A | 11/2000 | Uretsky | 6,315,721 | B2 | 11/2001 | Schulman et al. |
| 6,151,586 | A | 11/2000 | Brown | 6,319,540 | B1 | 11/2001 | Van Antwerp et al. |
| 6,153,062 | A | 11/2000 | Saito et al. | 6,326,160 | B1 | 12/2001 | Dunn et al. |
| 6,153,069 | A | 11/2000 | Pottgen et al. | 6,329,161 | B1 | 12/2001 | Heller et al. |
| 6,159,147 | A | 12/2000 | Lichter et al. | 6,329,929 | B1 | 12/2001 | Weijand et al. |
| 6,161,095 | A | 12/2000 | Brown | 6,330,426 | B2 | 12/2001 | Brown et al. |
| 6,162,611 | A | 12/2000 | Heller et al. | 6,330,464 | B1 | 12/2001 | Colvin, Jr. et al. |
| 6,162,639 | A | 12/2000 | Douglas | 6,331,518 | B2 | 12/2001 | Hemm et al. |
| 6,167,362 | A | 12/2000 | Brown et al. | 6,334,778 | B1 | 1/2002 | Brown |
| 6,168,563 | B1 | 1/2001 | Brown | 6,336,900 | B1 | 1/2002 | Alleckson et al. |
| 6,170,318 | B1 | 1/2001 | Lewis | 6,338,790 | B1 | 1/2002 | Feldman et al. |
| 6,175,752 | B1 | 1/2001 | Say et al. | 6,340,421 | B1 | 1/2002 | Vachon et al. |
| 6,180,416 | B1 | 1/2001 | Kurnik et al. | 6,341,232 | B1 | 1/2002 | Conn et al. |
| 6,186,145 | B1 | 2/2001 | Brown | 6,356,776 | B1 | 3/2002 | Berner et al. |
| 6,192,891 | B1 | 2/2001 | Gravel et al. | 6,360,888 | B1 | 3/2002 | McIvor et al. |
| 6,193,873 | B1 | 2/2001 | Ohara et al. | 6,366,793 | B1 | 4/2002 | Bell et al. |
| 6,196,970 | B1 | 3/2001 | Brown | 6,366,794 | B1 | 4/2002 | Moussy et al. |
| 6,198,957 | B1 | 3/2001 | Green | 6,368,141 | B1 | 4/2002 | Van Antwerp et al. |
| 6,200,265 | B1 | 3/2001 | Walsh et al. | 6,368,274 | B1 | 4/2002 | Van Antwerp et al. |
| 6,201,979 | B1 | 3/2001 | Kurnik et al. | 6,370,410 | B2 | 4/2002 | Kurnik et al. |
| 6,201,980 | B1 | 3/2001 | Darrow et al. | 6,377,828 | B1 | 4/2002 | Chaiken et al. |
| 6,206,841 | B1 | 3/2001 | Cunningham et al. | 6,379,301 | B1 | 4/2002 | Worthington et al. |
| 6,207,400 | B1 | 3/2001 | Kwon | 6,383,767 | B1 | 5/2002 | Polak |
| 6,208,894 | B1 | 3/2001 | Schulman et al. | 6,387,048 | B1 | 5/2002 | Schulman et al. |
| 6,210,272 | B1 | 4/2001 | Brown | 6,391,643 | B1 | 5/2002 | Chen et al. |
| 6,210,976 | B1 | 4/2001 | Sabbadini | 6,393,318 | B1 | 5/2002 | Conn et al. |
| 6,212,416 | B1 | 4/2001 | Ward et al. | 6,398,562 | B1 | 6/2002 | Butler et al. |
| 6,219,565 | B1 | 4/2001 | Cupp et al. | 6,405,066 | B1 | 6/2002 | Essenpreis et al. |
| 6,219,574 | B1 | 4/2001 | Cormier et al. | 6,413,393 | B1 | 7/2002 | Van Antwerp et al. |
| 6,224,745 | B1 | 5/2001 | Baltruschat | 6,418,332 | B1 | 7/2002 | Mastrototaro et al. |
| 6,232,130 | B1 | 5/2001 | Wolf | 6,424,847 | B1 | 7/2002 | Mastrototaro et al. |
| 6,232,370 | B1 | 5/2001 | Kubota et al. | 6,427,088 | B1 | 7/2002 | Bowman, IV et al. |
| 6,233,471 | B1 | 5/2001 | Berner et al. | 6,434,409 | B1 | 8/2002 | Pfeiffer et al. |
| 6,233,539 | B1 | 5/2001 | Brown | 6,438,414 | B1 | 8/2002 | Conn et al. |

| Patent No. | Date | Inventor |
|---|---|---|
| 6,440,068 B1 | 8/2002 | Brown et al. |
| 6,442,637 B1 | 8/2002 | Hawkins et al. |
| 6,443,942 B2 | 9/2002 | Van Antwerp et al. |
| 6,454,710 B1 | 9/2002 | Ballerstadt et al. |
| 6,462,162 B2 | 10/2002 | Van Antwerp et al. |
| 6,464,848 B1 | 10/2002 | Matsumoto |
| 6,466,810 B1 | 10/2002 | Ward et al. |
| 6,468,222 B1 | 10/2002 | Mault et al. |
| 6,472,122 B1 | 10/2002 | Schulman et al. |
| 6,475,750 B1 | 11/2002 | Han et al. |
| 6,477,395 B2 | 11/2002 | Schulman et al. |
| 6,478,736 B1 | 11/2002 | Mault |
| 6,480,730 B2 | 11/2002 | Darrow et al. |
| 6,482,158 B2 | 11/2002 | Mault |
| 6,482,604 B2 | 11/2002 | Kwon |
| 6,484,045 B1 | 11/2002 | Holker et al. |
| 6,484,046 B1 | 11/2002 | Say et al. |
| 6,485,138 B1 | 11/2002 | Kubota et al. |
| 6,494,830 B1 | 12/2002 | Wessel |
| 6,496,728 B2 | 12/2002 | Li et al. |
| 6,505,059 B1 | 1/2003 | Kollias et al. |
| 6,512,939 B1 | 1/2003 | Colvin et al. |
| 6,513,532 B2 | 2/2003 | Mault et al. |
| 6,514,718 B2 | 2/2003 | Heller et al. |
| 6,515,593 B1 | 2/2003 | Stark et al. |
| 6,520,326 B2 | 2/2003 | McIvor et al. |
| 6,529,755 B2 | 3/2003 | Kurnik et al. |
| 6,529,772 B2 | 3/2003 | Carlson et al. |
| 6,530,915 B1 | 3/2003 | Eppstein et al. |
| 6,534,322 B1 | 3/2003 | Sabbadini |
| 6,534,323 B1 | 3/2003 | Sabbadini |
| 6,535,753 B1 | 3/2003 | Raskas |
| 6,537,243 B1 | 3/2003 | Henning et al. |
| 6,540,675 B2 | 4/2003 | Aceti et al. |
| 6,544,212 B2 | 4/2003 | Galley et al. |
| 6,546,269 B1 | 4/2003 | Kurnik |
| 6,549,796 B2 | 4/2003 | Sohrab |
| 6,551,276 B1 | 4/2003 | Mann et al. |
| 6,551,494 B1 | 4/2003 | Heller et al. |
| 6,553,244 B2 | 4/2003 | Lesho et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,571,200 B1 | 5/2003 | Mault |
| 6,576,101 B1 | 6/2003 | Heller et al. |
| 6,576,117 B1 | 6/2003 | Iketaki et al. |
| 6,577,899 B2 | 6/2003 | Lebel et al. |
| 6,579,498 B1 | 6/2003 | Eglise |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,587,705 B1 | 7/2003 | Kim et al. |
| 6,591,125 B1 | 7/2003 | Buse et al. |
| 6,591,126 B2 | 7/2003 | Roeper et al. |
| 6,594,514 B2 | 7/2003 | Berner et al. |
| 6,595,919 B2 | 7/2003 | Berner et al. |
| 6,595,929 B2 | 7/2003 | Stivoric et al. |
| 6,602,678 B2 | 8/2003 | Kwon et al. |
| 6,602,909 B1 | 8/2003 | Jarowski |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,612,306 B1 | 9/2003 | Mault |
| 6,615,078 B1 | 9/2003 | Burson et al. |
| 6,618,603 B2 | 9/2003 | Varalli et al. |
| 6,620,106 B2 | 9/2003 | Mault |
| 6,627,058 B1 | 9/2003 | Chan |
| 6,629,934 B2 | 10/2003 | Mault et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,642,015 B2 | 11/2003 | Vachon et al. |
| 6,645,142 B2 | 11/2003 | Braig et al. |
| 6,648,821 B2 | 11/2003 | Lebel et al. |
| 6,653,091 B1 | 11/2003 | Dunn et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,671,554 B2 | 12/2003 | Gibson et al. |
| 6,673,625 B2 | 1/2004 | Satcher, Jr. et al. |
| 6,682,938 B1 | 1/2004 | Satcher, Jr. et al. |
| 6,683,040 B2 | 1/2004 | Bragulla et al. |
| 6,687,522 B2 | 2/2004 | Tamada |
| 6,687,546 B2 | 2/2004 | Lebel et al. |
| 6,689,056 B1 | 2/2004 | Kilcoyne et al. |
| 6,693,069 B2 | 2/2004 | Korber et al. |
| 6,694,158 B2 | 2/2004 | Polak |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,704,587 B1 | 3/2004 | Kumar et al. |
| 6,711,423 B2 | 3/2004 | Colvin, Jr. |
| 6,723,046 B2 | 4/2004 | Lichtenstein et al. |
| 6,728,560 B2 | 4/2004 | Kollias et al. |
| 6,731,976 B2 | 5/2004 | Penn et al. |
| 6,733,446 B2 | 5/2004 | Lebel et al. |
| 6,734,162 B2 | 5/2004 | Van Antwerp et al. |
| 6,736,777 B2 | 5/2004 | Kim et al. |
| 6,737,401 B2 | 5/2004 | Kim et al. |
| 6,738,654 B2 | 5/2004 | Sohrab |
| 6,740,075 B2 | 5/2004 | Lebel et al. |
| 6,741,163 B2 | 5/2004 | Roberts |
| 6,741,876 B1 | 5/2004 | Scecina et al. |
| 6,741,877 B1 | 5/2004 | Shults et al. |
| 6,746,582 B2 | 6/2004 | Heller et al. |
| 6,749,587 B2 | 6/2004 | Flaherty |
| 6,750,311 B1 | 6/2004 | Van Antwerp et al. |
| 6,758,810 B2 | 7/2004 | Lebel et al. |
| 6,766,183 B2 | 7/2004 | Walsh et al. |
| 6,766,201 B2 | 7/2004 | Von Arx et al. |
| 6,768,425 B2 | 7/2004 | Flaherty et al. |
| 6,770,030 B1 | 8/2004 | Schaupp et al. |
| 6,770,729 B2 | 8/2004 | Van Antwerp et al. |
| 6,771,995 B2 | 8/2004 | Kurnik et al. |
| 6,773,563 B2 | 8/2004 | Matsumoto |
| 6,780,297 B2 | 8/2004 | Matsumoto et al. |
| 6,780,871 B2 | 8/2004 | Glick et al. |
| 6,784,274 B2 | 8/2004 | Van Antwerp et al. |
| 6,790,178 B1 | 9/2004 | Mault et al. |
| 6,794,195 B2 | 9/2004 | Colvin, Jr. |
| 6,800,451 B2 | 10/2004 | Daniloff et al. |
| 6,804,544 B2 | 10/2004 | Van Antwerp et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,811,659 B2 | 11/2004 | Vachon |
| 6,812,031 B1 | 11/2004 | Carlsson |
| 6,813,519 B2 | 11/2004 | Lebel et al. |
| 6,816,742 B2 | 11/2004 | Kim et al. |
| 6,835,553 B2 | 12/2004 | Han et al. |
| RE38,681 E | 1/2005 | Kurnik et al. |
| 6,840,912 B2 | 1/2005 | Kloepfer et al. |
| 6,844,023 B2 | 1/2005 | Schulman et al. |
| 6,849,237 B2 | 2/2005 | Housefield et al. |
| 6,850,790 B2 | 2/2005 | Berner et al. |
| 6,852,500 B1 | 2/2005 | Hoss et al. |

| | | | |
|---|---|---|---|
| 6,852,694 B2 | 2/2005 | Van Antwerp et al. |
| 6,853,854 B1 | 2/2005 | Proniewicz et al. |
| 6,856,928 B2 | 2/2005 | Harmon |
| 6,858,403 B2 | 2/2005 | Han et al. |
| 6,862,465 B2 | 3/2005 | Shults et al. |
| 6,862,466 B2 | 3/2005 | Ackerman |
| 6,872,200 B2 | 3/2005 | Mann et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,885,883 B2 | 4/2005 | Parris et al. |
| 6,892,085 B2 | 5/2005 | McIvor et al. |
| 6,895,263 B2 | 5/2005 | Shin et al. |
| 6,895,265 B2 | 5/2005 | Silver |
| 6,899,683 B2 | 5/2005 | Mault et al. |
| 6,899,684 B2 | 5/2005 | Mault et al. |
| 6,902,905 B2 | 6/2005 | Burson et al. |
| 6,904,301 B2 | 6/2005 | Raskas |
| 6,907,127 B1 | 6/2005 | Kravitz et al. |
| 6,915,147 B2 | 7/2005 | Lebel et al. |
| 6,918,874 B1 | 7/2005 | Hatch et al. |
| 6,922,578 B2 | 7/2005 | Eppstein et al. |
| RE38,775 E | 8/2005 | Kurnik et al. |
| 6,923,764 B2 | 8/2005 | Aceti et al. |
| 6,923,936 B2 | 8/2005 | Swanson et al. |
| 6,927,246 B2 | 8/2005 | Noronha et al. |
| 6,931,327 B2 | 8/2005 | Goode, Jr. et al. |
| 6,936,006 B2 | 8/2005 | Sabra |
| 6,936,029 B2 | 8/2005 | Mann et al. |
| 6,940,590 B2 | 9/2005 | Colvin, Jr. et al. |
| 6,941,163 B2 | 9/2005 | Ford et al. |
| 6,950,708 B2 | 9/2005 | Bowman, IV et al. |
| 6,952,603 B2 | 10/2005 | Gerber et al. |
| 6,954,673 B2 | 10/2005 | Von Arx et al. |
| 6,955,650 B2 | 10/2005 | Mault et al. |
| 6,957,102 B2 | 10/2005 | Silver et al. |
| 6,957,107 B2 | 10/2005 | Rogers et al. |
| 6,958,705 B2 | 10/2005 | Lebel et al. |
| 6,968,294 B2 | 11/2005 | Gutta et al. |
| 6,968,375 B1 | 11/2005 | Brown |
| 6,971,274 B2 | 12/2005 | Olin |
| 6,974,437 B2 | 12/2005 | Lebel et al. |
| 6,978,182 B2 | 12/2005 | Mazar et al. |
| 6,979,326 B2 | 12/2005 | Mann et al. |
| 6,990,366 B2 | 1/2006 | Say et al. |
| 6,991,096 B2 | 1/2006 | Gottlieb et al. |
| 6,997,907 B2 | 2/2006 | Safabash et al. |
| 6,997,920 B2 | 2/2006 | Mann et al. |
| 6,998,247 B2 | 2/2006 | Monfre et al. |
| 6,999,810 B2 | 2/2006 | Berner et al. |
| 7,003,336 B2 | 2/2006 | Holker et al. |
| 7,003,340 B2 | 2/2006 | Say et al. |
| 7,003,341 B2 | 2/2006 | Say et al. |
| 7,004,901 B2 | 2/2006 | Fish |
| 7,005,857 B2 | 2/2006 | Stiene et al. |
| 7,011,630 B2 | 3/2006 | Desai et al. |
| 7,018,366 B2 | 3/2006 | Easter |
| 7,018,568 B2 | 3/2006 | Tierney |
| 7,022,072 B2 | 4/2006 | Fox et al. |
| 7,024,236 B2 | 4/2006 | Ford et al. |
| 7,024,245 B2 | 4/2006 | Lebel et al. |
| 7,025,743 B2 | 4/2006 | Mann et al. |
| 7,029,444 B2 | 4/2006 | Shin et al. |
| 7,039,810 B1 | 5/2006 | Nichols |
| 7,041,068 B2 | 5/2006 | Freeman et al. |
| 7,041,468 B2 | 5/2006 | Drucker et al. |
| 7,049,277 B2 | 5/2006 | Bagulla et al. |
| 7,052,472 B1 | 5/2006 | Miller et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,150,975 B2 | 12/2006 | Tamada et al. |
| 7,163,511 B2 | 1/2007 | Conn et al. |
| 7,171,274 B2 | 1/2007 | Starkweather et al. |
| 7,183,068 B2 | 2/2007 | Burson et al. |
| 7,183,102 B2 | 2/2007 | Monfre et al. |
| 7,189,341 B2 | 3/2007 | Li et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,226,978 B2 | 6/2007 | Tapsak et al. |
| 7,228,163 B2 | 6/2007 | Ackerman |
| 7,233,817 B2 | 6/2007 | Yen |
| 7,261,691 B1 | 8/2007 | Asomani |
| 7,276,029 B2 | 10/2007 | Goode, Jr. et al. |
| 7,295,867 B2 | 11/2007 | Berner et al. |
| 7,310,544 B2 | 12/2007 | Brister et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,632,228 B2 | 12/2009 | Brauker et al. |
| 2001/0011224 A1 | 8/2001 | Brown |
| 2001/0016310 A1 | 8/2001 | Brown et al. |
| 2001/0016682 A1 | 8/2001 | Berner et al. |
| 2001/0016683 A1 | 8/2001 | Darrow et al. |
| 2001/0020124 A1 | 9/2001 | Tamada |
| 2001/0029340 A1 | 10/2001 | Mault et al. |
| 2001/0032278 A1 | 10/2001 | Brown et al. |
| 2001/0037060 A1 | 11/2001 | Thompson et al. |
| 2001/0037069 A1 | 11/2001 | Carlson et al. |
| 2001/0039504 A1 | 11/2001 | Linberg et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0047125 A1 | 11/2001 | Quy |
| 2001/0049096 A1 | 12/2001 | Brown |
| 2001/0049470 A1 | 12/2001 | Mault et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0016530 A1 | 2/2002 | Brown |
| 2002/0019022 A1 | 2/2002 | Dunn et al. |
| 2002/0019586 A1 | 2/2002 | Teller et al. |
| 2002/0019748 A1 | 2/2002 | Brown |
| 2002/0026937 A1 | 3/2002 | Mault |
| 2002/0027164 A1 | 3/2002 | Mault et al. |
| 2002/0028995 A1 | 3/2002 | Mault |
| 2002/0040208 A1 | 4/2002 | Flaherty et al. |
| 2002/0042090 A1 | 4/2002 | Heller et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0063060 A1 | 5/2002 | Gascoyne et al. |
| 2002/0068858 A1 | 6/2002 | Braig et al. |
| 2002/0072858 A1 | 6/2002 | Cheng |

| | | | | | | |
|---|---|---|---|---|---|---|
| 2002/0077765 A1 | 6/2002 | Mault | | 2003/0232370 A1 | 12/2003 | Trifiro |
| 2002/0077766 A1 | 6/2002 | Mault | | 2003/0235817 A1 | 12/2003 | Bartkowiak et al. |
| 2002/0081559 A1 | 6/2002 | Brown et al. | | 2004/0010207 A1 | 1/2004 | Flaherty et al. |
| 2002/0083461 A1 | 6/2002 | Hutcheson et al. | | 2004/0011671 A1 | 1/2004 | Shults et al. |
| 2002/0087056 A1 | 7/2002 | Aceti et al. | | 2004/0018486 A1 | 1/2004 | Dunn et al. |
| 2002/0091312 A1 | 7/2002 | Berner et al. | | 2004/0039256 A1 | 2/2004 | Kawatahara et al. |
| 2002/0103425 A1 | 8/2002 | Mault | | 2004/0040840 A1 | 3/2004 | Mao et al. |
| 2002/0103499 A1 | 8/2002 | Perez et al. | | 2004/0045879 A1 | 3/2004 | Shults et al. |
| 2002/0106709 A1 | 8/2002 | Potts et al. | | 2004/0054263 A1 | 3/2004 | Moerman et al. |
| 2002/0107433 A1 | 8/2002 | Mault | | 2004/0059201 A1 | 3/2004 | Ginsberg |
| 2002/0107476 A1 | 8/2002 | Mann et al. | | 2004/0064068 A1 | 4/2004 | DeNuzzio et al. |
| 2002/0109600 A1 | 8/2002 | Mault et al. | | 2004/0069164 A1 | 4/2004 | Nakamura et al. |
| 2002/0119711 A1 | 8/2002 | Van Antwerp et al. | | 2004/0072357 A1 | 4/2004 | Stiene et al. |
| 2002/0124017 A1 | 9/2002 | Mault | | 2004/0073095 A1 | 4/2004 | Causey, III et al. |
| 2002/0128594 A1 | 9/2002 | Das et al. | | 2004/0096959 A1 | 5/2004 | Stiene et al. |
| 2002/0130042 A1 | 9/2002 | Moerman et al. | | 2004/0106858 A1 | 6/2004 | Say et al. |
| 2002/0133378 A1 | 9/2002 | Mault et al. | | 2004/0108226 A1 | 6/2004 | Polychronakos et al. |
| 2002/0161286 A1 | 10/2002 | Gerber et al. | | 2004/0122353 A1 | 6/2004 | Shahmirian et al. |
| 2002/0161288 A1 | 10/2002 | Shin et al. | | 2004/0122489 A1 | 6/2004 | Mazar et al. |
| 2002/0177764 A1 | 11/2002 | Sohrab | | 2004/0133164 A1 | 7/2004 | Funderburk et al. |
| 2003/0023182 A1 | 1/2003 | Mault et al. | | 2004/0138588 A1 | 7/2004 | Saikley et al. |
| 2003/0023317 A1 | 1/2003 | Brauker et al. | | 2004/0152622 A1* | 8/2004 | Keith et al. .................. 514/3 |
| 2003/0028089 A1* | 2/2003 | Galley et al. ................ 600/365 | | 2004/0153585 A1 | 8/2004 | Kawatahara et al. |
| 2003/0028120 A1 | 2/2003 | Mault et al. | | 2004/0162473 A1 | 8/2004 | Sohrab |
| 2003/0032077 A1 | 2/2003 | Itoh et al. | | 2004/0164961 A1 | 8/2004 | Bal et al. |
| 2003/0032867 A1 | 2/2003 | Crothall et al. | | 2004/0167383 A1 | 8/2004 | Kim et al. |
| 2003/0032868 A1 | 2/2003 | Graskov et al. | | 2004/0167801 A1 | 8/2004 | Say et al. |
| 2003/0032874 A1 | 2/2003 | Rhodes et al. | | 2004/0171921 A1 | 9/2004 | Say et al. |
| 2003/0040683 A1 | 2/2003 | Rule et al. | | 2004/0172284 A1 | 9/2004 | Sullivan et al. |
| 2003/0042137 A1 | 3/2003 | Mao et al. | | 2004/0176672 A1 | 9/2004 | Silver et al. |
| 2003/0050537 A1 | 3/2003 | Wessel | | 2004/0176913 A1 | 9/2004 | Kawatahara et al. |
| 2003/0050546 A1 | 3/2003 | Desai et al. | | 2004/0186362 A1 | 9/2004 | Brauker et al. |
| 2003/0065257 A1 | 4/2003 | Mault et al. | | 2004/0186365 A1 | 9/2004 | Jin et al. |
| 2003/0065273 A1 | 4/2003 | Mault et al. | | 2004/0193025 A1 | 9/2004 | Steil et al. |
| 2003/0065274 A1 | 4/2003 | Mault et al. | | 2004/0193090 A1 | 9/2004 | Lebel et al. |
| 2003/0065275 A1 | 4/2003 | Mault et al. | | 2004/0199059 A1 | 10/2004 | Brauker et al. |
| 2003/0065308 A1 | 4/2003 | Lebel et al. | | 2004/0202576 A1 | 10/2004 | Aceti et al. |
| 2003/0100040 A1 | 5/2003 | Bonnecaze et al. | | 2004/0204687 A1 | 10/2004 | Mogensen et al. |
| 2003/0100821 A1 | 5/2003 | Heller et al. | | 2004/0225338 A1 | 11/2004 | Lebel et al. |
| 2003/0105407 A1 | 6/2003 | Pearce et al. | | 2004/0248204 A1 | 12/2004 | Moerman |
| 2003/0108976 A1 | 6/2003 | Braig et al. | | 2004/0249250 A1 | 12/2004 | McGee et al. |
| 2003/0130616 A1 | 7/2003 | Steil et al. | | 2004/0249253 A1 | 12/2004 | Racchini et al. |
| 2003/0134347 A1 | 7/2003 | Heller et al. | | 2004/0249254 A1 | 12/2004 | Racchini et al. |
| 2003/0135100 A1 | 7/2003 | Kim et al. | | 2004/0249999 A1 | 12/2004 | Connolly et al. |
| 2003/0135333 A1 | 7/2003 | Aceti et al. | | 2004/0253736 A1 | 12/2004 | Stout et al. |
| 2003/0153820 A1 | 8/2003 | Berner et al. | | 2004/0254429 A1 | 12/2004 | Yang |
| 2003/0153821 A1 | 8/2003 | Berner et al. | | 2004/0254433 A1 | 12/2004 | Bandis et al. |
| 2003/0158472 A1 | 8/2003 | Sohrab | | 2004/0254434 A1 | 12/2004 | Goodnow et al. |
| 2003/0158707 A1 | 8/2003 | Doi | | 2004/0260363 A1 | 12/2004 | Arx et al. |
| 2003/0168338 A1 | 9/2003 | Gao et al. | | 2004/0263354 A1 | 12/2004 | Mann et al. |
| 2003/0175806 A1 | 9/2003 | Rule et al. | | 2004/0267300 A1 | 12/2004 | Mace |
| 2003/0176183 A1 | 9/2003 | Drucker et al. | | 2005/0003470 A1 | 1/2005 | Nelson et al. |
| 2003/0176933 A1 | 9/2003 | Lebel et al. | | 2005/0004494 A1 | 1/2005 | Perez et al. |
| 2003/0181851 A1 | 9/2003 | Mann et al. | | 2005/0010087 A1 | 1/2005 | Banet et al. |
| 2003/0181852 A1 | 9/2003 | Mann et al. | | 2005/0010269 A1 | 1/2005 | Lebel et al. |
| 2003/0187338 A1 | 10/2003 | Say et al. | | 2005/0027177 A1 | 2/2005 | Shin et al. |
| 2003/0187525 A1 | 10/2003 | Mann et al. | | 2005/0027179 A1 | 2/2005 | Berner et al. |
| 2003/0191376 A1 | 10/2003 | Samuels et al. | | 2005/0027180 A1 | 2/2005 | Goode, Jr. et al. |
| 2003/0191431 A1 | 10/2003 | Mann et al. | | 2005/0027181 A1 | 2/2005 | Goode, Jr. et al. |
| 2003/0195403 A1 | 10/2003 | Berner et al. | | 2005/0027462 A1 | 2/2005 | Goode, Jr. et al. |
| 2003/0195462 A1 | 10/2003 | Mann et al. | | 2005/0027463 A1 | 2/2005 | Goode, Jr. et al. |
| 2003/0199790 A1 | 10/2003 | Boecker et al. | | 2005/0031689 A1 | 2/2005 | Shults et al. |
| 2003/0199791 A1 | 10/2003 | Boecker et al. | | 2005/0033132 A1 | 2/2005 | Shults et al. |
| 2003/0199903 A1 | 10/2003 | Boecker et al. | | 2005/0038680 A1 | 2/2005 | McMahon |
| 2003/0208110 A1 | 11/2003 | Mault et al. | | 2005/0043598 A1 | 2/2005 | Goode, Jr. et al. |
| 2003/0208113 A1 | 11/2003 | Mault et al. | | 2005/0043894 A1 | 2/2005 | Fernandez |
| 2003/0208133 A1 | 11/2003 | Mault | | 2005/0049473 A1 | 3/2005 | Desai et al. |
| 2003/0208409 A1 | 11/2003 | Mault | | 2005/0054909 A1 | 3/2005 | Petisce et al. |
| 2003/0212364 A1 | 11/2003 | Mann et al. | | 2005/0090607 A1 | 4/2005 | Tapsak et al. |
| 2003/0212379 A1 | 11/2003 | Bylund et al. | | 2005/0112169 A1 | 5/2005 | Brauker et al. |
| 2003/0217966 A1 | 11/2003 | Tapsak et al. | | 2005/0113657 A1 | 5/2005 | Alarcon et al. |
| 2003/0226695 A1 | 12/2003 | Mault | | 2005/0113658 A1 | 5/2005 | Jacobson et al. |
| 2003/0229514 A2 | 12/2003 | Brown | | 2005/0114068 A1 | 5/2005 | Chey et al. |

| | | | | | |
|---|---|---|---|---|---|
| 2005/0118726 A1 | 6/2005 | Schultz et al. | 2006/0189863 A1 | 8/2006 | Peyser et al. |
| 2005/0121322 A1 | 6/2005 | Say et al. | 2006/0195029 A1 | 8/2006 | Shults et al. |
| 2005/0124873 A1 | 6/2005 | Shults et al. | 2006/0222566 A1 | 10/2006 | Brauker et al. |
| 2005/0131346 A1 | 6/2005 | Douglas | 2006/0247985 A1 | 11/2006 | Liamos et al. |
| 2005/0137471 A1 | 6/2005 | Haar et al. | 2007/0016381 A1 | 1/2007 | Kamath et al. |
| 2005/0143635 A1 | 6/2005 | Kamath et al. | 2007/0027381 A1 | 2/2007 | Stafford |
| 2005/0143636 A1 | 6/2005 | Zhang et al. | 2007/0060814 A1 | 3/2007 | Stafford |
| 2005/0148003 A1 | 7/2005 | Keith et al. | 2007/0073129 A1 | 3/2007 | Shah et al. |
| 2005/0154271 A1 | 7/2005 | Rasdal et al. | 2007/0078320 A1 | 4/2007 | Stafford |
| 2005/0161346 A1 | 7/2005 | Simpson et al. | 2007/0078321 A1 | 4/2007 | Mazza et al. |
| 2005/0171503 A1 | 8/2005 | Van Den Berghe et al. | 2007/0078322 A1 | 4/2007 | Stafford |
| 2005/0171513 A1 | 8/2005 | Mann et al. | 2007/0106135 A1 | 5/2007 | Sloan et al. |
| 2005/0173245 A1 | 8/2005 | Feldman et al. | 2007/0149873 A1 | 6/2007 | Say et al. |
| 2005/0176136 A1 | 8/2005 | Burd et al. | 2007/0149874 A1 | 6/2007 | Say et al. |
| 2005/0177036 A1 | 8/2005 | Shults et al. | 2007/0151869 A1 | 7/2007 | Heller et al. |
| 2005/0181012 A1 | 8/2005 | Saint et al. | 2007/0161879 A1 | 7/2007 | Say et al. |
| 2005/0182306 A1 | 8/2005 | Sloan et al. | 2007/0161880 A1 | 7/2007 | Say et al. |
| 2005/0182451 A1 | 8/2005 | Griffin et al. | 2007/0163880 A1 | 7/2007 | Woo et al. |
| 2005/0187720 A1 | 8/2005 | Goode, Jr. et al. | 2007/0173706 A1 | 7/2007 | Neinast et al. |
| 2005/0192557 A1 | 9/2005 | Brauker et al. | 2007/0179370 A1 | 8/2007 | Say et al. |
| 2005/0195930 A1 | 9/2005 | Spital et al. | 2007/0179372 A1 | 8/2007 | Say et al. |
| 2005/0199494 A1 | 9/2005 | Say et al. | 2007/0191699 A1 | 8/2007 | Say et al. |
| 2005/0203360 A1* | 9/2005 | Brauker et al. ............... 600/345 | 2007/0191700 A1 | 8/2007 | Say et al. |
| 2005/0203707 A1 | 9/2005 | Tsutsui et al. | 2007/0203408 A1 | 8/2007 | Say et al. |
| 2005/0214892 A1 | 9/2005 | Kovatchev et al. | 2007/0203410 A1 | 8/2007 | Say et al. |
| 2005/0215871 A1 | 9/2005 | Feldman et al. | 2007/0203411 A1 | 8/2007 | Say et al. |
| 2005/0215872 A1 | 9/2005 | Berner et al. | 2007/0203966 A1 | 8/2007 | Brauker et al. |
| 2005/0239154 A1 | 10/2005 | Feldman et al. | 2007/0208247 A1 | 9/2007 | Say et al. |
| 2005/0239156 A1 | 10/2005 | Drucker et al. | 2007/0213610 A1 | 9/2007 | Say et al. |
| 2005/0245795 A1 | 11/2005 | Goode, Jr. et al. | 2007/0215491 A1 | 9/2007 | Heller et al. |
| 2005/0245799 A1 | 11/2005 | Brauker et al. | 2007/0218097 A1 | 9/2007 | Heller et al. |
| 2005/0251083 A1 | 11/2005 | Carr-Brendel et al. | 2007/0235331 A1 | 10/2007 | Simpson et al. |
| 2005/0261660 A1 | 11/2005 | Choi | 2007/0244380 A1 | 10/2007 | Say et al. |
| 2005/0267780 A1 | 12/2005 | Ray et al. | 2007/0249919 A1 | 10/2007 | Say et al. |
| 2005/0271546 A1 | 12/2005 | Gerber et al. | 2007/0249920 A1 | 10/2007 | Say et al. |
| 2005/0271547 A1 | 12/2005 | Gerber et al. | 2007/0249922 A1 | 10/2007 | Peyser et al. |
| 2005/0272640 A1 | 12/2005 | Doyle, III et al. | 2008/0009692 A1 | 1/2008 | Stafford |
| 2005/0272985 A1 | 12/2005 | Kotulla et al. | 2008/0021666 A1 | 1/2008 | Goode, Jr. et al. |
| 2005/0277164 A1 | 12/2005 | Drucker et al. | 2008/0033254 A1 | 2/2008 | Kamath et al. |
| 2005/0287620 A1 | 12/2005 | Heller et al. | 2008/0039702 A1 | 2/2008 | Hayter et al. |
| 2006/0001538 A1 | 1/2006 | Kraft et al. | 2008/0045824 A1 | 2/2008 | Tapsak et al. |
| 2006/0001550 A1 | 1/2006 | Mann et al. | 2008/0071156 A1 | 3/2008 | Brister et al. |
| 2006/0001551 A1 | 1/2006 | Kraft et al. | 2008/0083617 A1 | 4/2008 | Simpson et al. |
| 2006/0003398 A1 | 1/2006 | Heller et al. | 2008/0086042 A1 | 4/2008 | Brister et al. |
| 2006/0004271 A1 | 1/2006 | Peyser et al. | 2008/0086044 A1 | 4/2008 | Brister et al. |
| 2006/0007017 A1 | 1/2006 | Mann et al. | 2008/0086273 A1 | 4/2008 | Shults et al. |
| 2006/0015020 A1 | 1/2006 | Neale et al. | 2008/0108942 A1 | 5/2008 | Brister et al. |
| 2006/0015024 A1 | 1/2006 | Brister et al. | 2008/0183061 A1 | 7/2008 | Goode et al. |
| 2006/0016700 A1 | 1/2006 | Brister et al. | 2008/0183399 A1 | 7/2008 | Goode et al. |
| 2006/0019327 A1 | 1/2006 | Brister et al. | 2008/0188731 A1 | 8/2008 | Brister et al. |
| 2006/0020186 A1 | 1/2006 | Brister et al. | 2008/0189051 A1 | 8/2008 | Goode et al. |
| 2006/0020187 A1 | 1/2006 | Brister et al. | 2008/0194935 A1 | 8/2008 | Brister et al. |
| 2006/0020188 A1 | 1/2006 | Kamath et al. | 2008/0194936 A1 | 8/2008 | Goode et al. |
| 2006/0020189 A1 | 1/2006 | Brister et al. | 2008/0194937 A1 | 8/2008 | Goode et al. |
| 2006/0020190 A1 | 1/2006 | Kamath et al. | 2008/0194938 A1 | 8/2008 | Brister et al. |
| 2006/0020191 A1 | 1/2006 | Brister et al. | 2008/0195232 A1 | 8/2008 | Carr-Brendel et al. |
| 2006/0020192 A1 | 1/2006 | Brister et al. | 2008/0195967 A1 | 8/2008 | Goode et al. |
| 2006/0025663 A1 | 2/2006 | Talbot et al. | 2008/0197024 A1 | 8/2008 | Simpson et al. |
| 2006/0031094 A1 | 2/2006 | Cohen et al. | 2008/0200788 A1 | 8/2008 | Brister et al. |
| 2006/0036139 A1 | 2/2006 | Brister et al. | 2008/0200789 A1 | 8/2008 | Brister et al. |
| 2006/0036140 A1 | 2/2006 | Brister et al. | 2008/0200791 A1 | 8/2008 | Simpson et al. |
| 2006/0036141 A1 | 2/2006 | Kamath et al. | 2008/0208025 A1 | 8/2008 | Shults et al. |
| 2006/0036142 A1 | 2/2006 | Brister et al. | 2008/0214915 A1 | 9/2008 | Brister et al. |
| 2006/0036143 A1 | 2/2006 | Brister et al. | 2008/0214918 A1 | 9/2008 | Brister et al. |
| 2006/0036144 A1 | 2/2006 | Brister et al. | 2008/0228051 A1 | 9/2008 | Shults et al. |
| 2006/0036145 A1 | 2/2006 | Brister et al. | 2008/0228054 A1 | 9/2008 | Shults et al. |
| 2006/0036187 A1 | 2/2006 | Vos et al. | 2008/0242961 A1 | 10/2008 | Brister et al. |
| 2006/0040402 A1 | 2/2006 | Brauker et al. | 2008/0262469 A1 | 10/2008 | Brister et al. |
| 2006/0052679 A1 | 3/2006 | Kotulla et al. | 2008/0275313 A1 | 11/2008 | Brister et al. |
| 2006/0058602 A1 | 3/2006 | Kwiatkowski et al. | 2008/0287764 A1 | 11/2008 | Rasdal et al. |
| 2006/0063218 A1 | 3/2006 | Bartkowiak et al. | 2008/0287765 A1 | 11/2008 | Rasdal et al. |
| 2006/0074564 A1 | 4/2006 | Bartowiak et al. | 2008/0287766 A1 | 11/2008 | Rasdal et al. |
| 2006/0173444 A1 | 8/2006 | Choy et al. | 2008/0296155 A1 | 12/2008 | Shults et al. |

| Pub. No. | Date | Inventors | Country | Number | Date |
|---|---|---|---|---|---|
| 2008/0306368 A1 | 12/2008 | Goode et al. | EP | 0136362 | 4/1985 |
| 2008/0306434 A1 | 12/2008 | Dobbles et al. | EP | 0170375 | 2/1986 |
| 2008/0306435 A1 | 12/2008 | Kamath et al. | EP | 0177743 | 4/1986 |
| 2008/0306444 A1 | 12/2008 | Brister et al. | EP | 0184909 | 6/1986 |
| 2009/0012379 A1 | 1/2009 | Goode et al. | EP | 0206218 | 12/1986 |
| 2009/0018424 A1 | 1/2009 | Kamath et al. | EP | 0230472 | 8/1987 |
| 2009/0030294 A1 | 1/2009 | Petisce et al. | EP | 0241309 | 10/1987 |
| 2009/0036758 A1 | 2/2009 | Brauker et al. | EP | 0245073 | 11/1987 |
| 2009/0036763 A1 | 2/2009 | Brauker et al. | EP | 0255291 | 2/1988 |
| 2009/0043181 A1 | 2/2009 | Brauker et al. | EP | 0278647 | 8/1988 |
| 2009/0043182 A1 | 2/2009 | Brauker et al. | EP | 0320109 | 6/1989 |
| 2009/0043525 A1 | 2/2009 | Brauker et al. | EP | 0353328 | 2/1990 |
| 2009/0043541 A1 | 2/2009 | Brauker et al. | EP | 0359831 | 3/1990 |
| 2009/0043542 A1 | 2/2009 | Brauker et al. | EP | 0368209 | 5/1990 |
| 2009/0045055 A1 | 2/2009 | Rhodes et al. | EP | 0368290 | 5/1990 |
| 2009/0062633 A1 | 3/2009 | Brauker et al. | EP | 0390390 | 10/1990 |
| 2009/0062635 A1 | 3/2009 | Brauker et al. | EP | 0396788 | 11/1990 |
| 2009/0076356 A1 | 3/2009 | Simpson et al. | EP | 0400918 | 12/1990 |
| 2009/0076360 A1 | 3/2009 | Brister et al. | EP | 0453283 | 10/1991 |
| 2009/0076361 A1 | 3/2009 | Kamath et al. | EP | 0470290 | 2/1992 |
| 2009/0099436 A1 | 4/2009 | Brister et al. | EP | 0504835 | 9/1992 |
| 2009/0124877 A1 | 5/2009 | Goode et al. | EP | 0286118 | 1/1995 |
| 2009/0124878 A1 | 5/2009 | Goode et al. | EP | 0653718 | 5/1995 |
| 2009/0124879 A1 | 5/2009 | Brister et al. | EP | 0800082 | 10/1997 |
| 2009/0124964 A1 | 5/2009 | Leach et al. | EP | 0880936 | 12/1998 |
| 2009/0131768 A1 | 5/2009 | Simpson et al. | EP | 0970655 | 1/2000 |
| 2009/0131769 A1 | 5/2009 | Leach et al. | EP | 1034734 | 9/2000 |
| 2009/0131776 A1 | 5/2009 | Simpson et al. | EP | 1048264 | 11/2000 |
| 2009/0131777 A1 | 5/2009 | Simpson et al. | EP | 1445746 | 8/2004 |
| 2009/0137886 A1 | 5/2009 | Shariati et al. | GB | 1394171 | 5/1975 |
| 2009/0137887 A1 | 5/2009 | Shariati et al. | GB | 1579690 | 11/1980 |
| 2009/0143659 A1 | 6/2009 | Li et al. | GB | 1599241 | 9/1981 |
| 2009/0143660 A1 | 6/2009 | Brister et al. | GB | 2073891 | 10/1981 |
| 2009/0156919 A1 | 6/2009 | Brister et al. | GB | 2154003 | 8/1985 |
| 2009/0156924 A1 | 6/2009 | Shariati et al. | GB | 2194892 | 3/1988 |
| 2009/0163790 A1 | 6/2009 | Brister et al. | GB | 2204408 | 11/1988 |
| 2009/0163791 A1 | 6/2009 | Brister et al. | GB | 2225637 | 6/1990 |
| 2009/0178459 A1 | 7/2009 | Li et al. | GB | 2254436 | 10/1992 |
| 2009/0182217 A1 | 7/2009 | Li et al. | JP | 54-041191 | 4/1979 |
| 2009/0192366 A1 | 7/2009 | Mensinger et al. | JP | 55-012406 | 1/1980 |
| 2009/0192380 A1 | 7/2009 | Shariati et al. | JP | 56-163447 | 12/1981 |
| 2009/0192722 A1 | 7/2009 | Shariati et al. | JP | 57-070448 | 4/1982 |
| 2009/0192724 A1 | 7/2009 | Brauker et al. | JP | 60-173457 | 9/1985 |
| 2009/0192745 A1 | 7/2009 | Kamath et al. | JP | 60-173458 | 9/1985 |
| 2009/0192751 A1 | 7/2009 | Kamath et al. | JP | 60-173459 | 9/1985 |
| 2009/0203981 A1 | 8/2009 | Brauker et al. | JP | 61-090050 | 5/1986 |
| 2009/0204341 A1 | 8/2009 | Brauker et al. | JP | 62-085855 | 4/1987 |
| 2009/0216103 A1 | 8/2009 | Brister et al. | JP | 62-114747 | 5/1987 |
| 2009/0240120 A1 | 9/2009 | Mensinger et al. | JP | 63-058149 | 3/1988 |
| 2009/0240128 A1 | 9/2009 | Mensinger et al. | JP | 63-128252 | 5/1988 |
| 2009/0240193 A1 | 9/2009 | Mensinger et al. | JP | 63-139246 | 6/1988 |
| 2009/0242399 A1 | 10/2009 | Kamath et al. | JP | 63-294799 | 12/1988 |
| 2009/0242425 A1 | 10/2009 | Kamath et al. | JP | 63-317757 | 12/1988 |
| 2009/0247855 A1 | 10/2009 | Boock et al. | JP | 63-317758 | 12/1988 |
| 2009/0247856 A1 | 10/2009 | Boock et al. | JP | 1-114746 | 5/1989 |
| 2009/0287073 A1 | 11/2009 | Boock et al. | JP | 1-114747 | 5/1989 |
| 2009/0287074 A1 | 11/2009 | Shults et al. | JP | 1-124060 | 5/1989 |
| 2009/0299155 A1 | 12/2009 | Yang et al. | JP | 1-134244 | 5/1989 |
| 2009/0299156 A1 | 12/2009 | Simpson et al. | JP | 1-156658 | 6/1989 |
| 2009/0299162 A1 | 12/2009 | Brauker et al. | JP | 2-062958 | 3/1990 |
| 2009/0299276 A1 | 12/2009 | Brauker et al. | JP | 2-120655 | 5/1990 |
| | | | JP | 2-287145 | 11/1990 |
| | FOREIGN PATENT DOCUMENTS | | JP | 2-310457 | 12/1990 |
| | | | JP | 3-026956 | 2/1991 |
| EP | 0010375 | 4/1980 | JP | 3-028752 | 2/1991 |
| EP | 1579690 | 11/1980 | JP | 3-202764 | 9/1991 |
| EP | 0026995 | 4/1981 | JP | 5-072171 | 3/1993 |
| EP | 0048090 | 3/1982 | JP | 5-196595 | 8/1993 |
| EP | 0078636 | 5/1983 | JP | 6-190050 | 7/1994 |
| EP | 0080304 | 6/1983 | JP | 7-055757 | 3/1995 |
| EP | 0098592 | 1/1984 | JP | 7-072585 | 3/1995 |
| EP | 0125139 | 11/1984 | JP | 8-154903 | 6/1996 |
| EP | 0127958 | 12/1984 | JP | 8-285814 | 11/1996 |

| | | |
|---|---|---|
| JP | 8-285815 | 11/1996 |
| JP | 9-021778 | 1/1997 |
| JP | 9-101280 | 4/1997 |
| JP | 9-285459 | 11/1997 |
| JP | 10-170471 | 6/1998 |
| JP | 2000-000231 | 1/2000 |
| JP | 2000-116628 | 4/2000 |
| WO | WO-85/05119 | 11/1985 |
| WO | WO-86/00513 | 1/1986 |
| WO | WO-87/00513 | 1/1987 |
| WO | WO-87/06040 | 10/1987 |
| WO | WO-89/02246 | 3/1989 |
| WO | WO-89/05119 | 6/1989 |
| WO | WO-89/08713 | 9/1989 |
| WO | WO-90/00367 | 1/1990 |
| WO | WO-90/05300 | 5/1990 |
| WO | WO-90/05910 | 5/1990 |
| WO | WO-91/01680 | 2/1991 |
| WO | WO-91/04704 | 4/1991 |
| WO | WO-91/15993 | 10/1991 |
| WO | WO-92/13271 | 8/1992 |
| WO | WO-94/20602 | 9/1994 |
| WO | WO-94/27140 | 11/1994 |
| WO | WO-95/06240 | 3/1995 |
| WO | WO-96/07908 | 3/1996 |
| WO | WO-96/25089 | 8/1996 |
| WO | WO-96/30431 | 10/1996 |
| WO | WO-96/35370 | 11/1996 |
| WO | WO-97/02847 | 1/1997 |
| WO | WO-97/19344 | 5/1997 |
| WO | WO-97/20207 | 6/1997 |
| WO | WO-97/41421 | 11/1997 |
| WO | WO-97/42882 | 11/1997 |
| WO | WO-97/42883 | 11/1997 |
| WO | WO-97/42886 | 11/1997 |
| WO | WO-97/42888 | 11/1997 |
| WO | WO-97/43962 | 11/1997 |
| WO | WO-97/46868 | 12/1997 |
| WO | WO-98/09167 | 3/1998 |
| WO | WO-98/24366 | 6/1998 |
| WO | WO-98/35053 | 8/1998 |
| WO | WO-98/52045 | 11/1998 |
| WO | WO-98/52293 | 11/1998 |
| WO | WO-99/05966 | 2/1999 |
| WO | WO-99/32883 | 7/1999 |
| WO | WO-99/56613 | 11/1999 |
| WO | WO-00/13580 | 3/2000 |
| WO | WO-00/18294 | 4/2000 |
| WO | WO-00/19887 | 4/2000 |
| WO | WO-00/20626 | 4/2000 |
| WO | WO-00/33065 | 6/2000 |
| WO | WO-00/49940 | 8/2000 |
| WO | WO-00/59370 | 10/2000 |
| WO | WO-00/62664 | 10/2000 |
| WO | WO-00/62665 | 10/2000 |
| WO | WO-00/78210 | 12/2000 |
| WO | WO-00/78992 | 12/2000 |
| WO | WO-01/24038 | 4/2001 |
| WO | WO-01/33216 | 5/2001 |
| WO | WO-01/52727 | 7/2001 |
| WO | WO-01/52935 | 7/2001 |
| WO | WO-01/54753 | 8/2001 |
| WO | WO-01/57238 | 8/2001 |
| WO | WO-01/57239 | 8/2001 |
| WO | WO-01/67009 | 9/2001 |
| WO | WO-02/13686 | 2/2002 |
| WO | WO-02/16905 | 2/2002 |
| WO | WO-02/17210 | 2/2002 |
| WO | WO-02/058537 | 8/2002 |
| WO | WO-02/078512 | 10/2002 |
| WO | WO-03/036583 | 5/2003 |
| WO | WO-03/076893 | 9/2003 |
| WO | WO-03/082091 | 10/2003 |
| WO | WO-2004/061420 | 7/2004 |
| WO | WO-2005/089103 | 9/2005 |
| WO | WO-2006/119084 | 11/2006 |
| WO | WO-2007/002189 | 1/2007 |
| WO | WO-2007/016399 | 2/2007 |
| WO | WO-2007/027381 | 3/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/053832 | 5/2007 |
| WO | WO-2007/056638 | 5/2007 |
| WO | WO-2007/120363 | 10/2007 |
| WO | WO-2007/143225 | 12/2007 |

OTHER PUBLICATIONS

Abruna, H. D., et al., "Rectifying Interfaces Using Two-Layer Films of Electrochemically Polymerized Vinylpyridine and Vinylbipyridine Complexes of Ruthenium and Iron on Electrodes", *Journal of the American Chemical Society*, vol. 103, No. 1, 1981, pp. 1-5.

Albery, W. J., et al., "Amperometric Enzyme Electrodes Part II: Conducting Salts as Electrode Materials for the Oxidation of Glucose Oxidase", *Journal of ElectroAnalytical Chemistry*, vol. 194, 1985, pp. 223-235.

Albery, W. J., et al., "Amperometric Enzyme Electrodes", *Philosophical Transactions of The Royal Society of London*, vol. 316, 1987, pp. 107-119.

Alcock, S. J., et al., "Continuous Analyte Monitoring to Aid Clinical Practice", *IEEE Engineering in Medicine and Biology Magazine*, 1994, pp. 319-325.

Anderson, L. B., et al., "Thin-Layer Electrochemistry: Steady-State Methods of Studying Rate Processes", *Journal of ElectroAnalytical Chemistry*, vol. 10, 1965, pp. 295-305.

Armour, J. C., et al., "Application of Chronic Intravascular Blood Glucose Sensor in Dogs", *Diabetes*, vol. 39, 1990, pp. 1519-1526.

Bartlett, P. N., et al., "Covalent Binding of Electron Relays to Glucose Oxidase", *Journal of the Chemical Society, Chemical Communications*, 1987, pp. 1603-1604.

Bartlett, P. N., et al., "Modification of Glucose Oxidase by Tetrathiafulvalene", *Journal of the Chemical Society, Chemical Communications*, 1990, pp. 1135-1136.

Bartlett, P. N., et al., "Strategies for the Development of Amperometric Enzyme Electrodes", *Biosensors*, vol. 3, 1987/88, pp. 359-379.

Bennion, N., et al., "Alternate Site Glucose Testing: A Crossover Design", *Diabetes Technology & Therapeutics*, vol. 4, No. 1, 2002, pp. 25-33.

Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.

Boedeker Plastics, Inc., "Polyethylene Specifications", Web Page of Boedeker.com, 2007, pp. 1-3.

Brandt, J., et al., "Covalent Attachment of Proteins to Polysaccharide Carriers by Means of Benzoquinone", *Biochimica et Biophysica Acta*, vol. 386, 1975, pp. 196-202.

Brooks, S. L., et al., "Development of an On-Line Glucose Sensor for Fermentation Monitoring", *Biosensors*, vol. 3, 1987/88, pp. 45-56.

Brownlee, M., et al., "A Glucose-Controlled Insulin-Delivery System: Semisynthetic Insulin Bound to Lectin", *Science*, vol. 206, 1979, 1190-1191.

Cass, A. E., et al., "Ferricinum Ion As An Electron Acceptor for Oxido-Reductases", *Journal of ElectroAnalytical Chemistry*, vol. 190, 1985, pp. 117-127.

Cass, A. E., et al., "Ferrocene-Medicated Enzyme Electrode for Amperometric Determination of Glucose", *Analytical Chemistry*, vol. 56, No. 4, 1984, 667-671.

Castner, J. F., et al., "Mass Transport and Reaction Kinetic Parameters Determined Electrochemically for Immobilized Glucose Oxidase", *Biochemistry*, vol. 23 No. 10, 1984, 2203-2210.

Claremont, D. J., et al., "Biosensors for Continuous in Vivo Glucose Monitoring", *Proceedings of the Annual International Conference of the IEEE Engineering in Medicine and Biology Society*, vol. 10, 1988.

Clark Jr., L. C., et al., "Differential Anodic Enzyme Polarography for the Measurement of Glucose", *Oxygen Transport to Tissue: Instrumentation, Methods, and Physiology*, 1973, pp. 127-133.

Clark Jr., L. C., et al., "Electrode Systems for Continuous Monitoring in Cardiovascular Surgery", *Annals New York Academy of Sciences*, 1962, pp. 29-45.

Clark Jr., L. C., et al., "Long-term Stability of Electroenzymatic Glucose Sensors Implanted in Mice", *American Society of Artificial Internal Organs Transactions*, vol. XXXIV, 1988, pp. 259-265.

Clarke, W. L., et al., "Evaluating Clinical Accuracy of Systems for Self-Monitoring of Blood Glucose", *Diabetes Care*, vol. 10, No. 5, 1987, pp. 622-628.

Complaint, "*Abbott Diabetes Care, Inc. v. Dexcom, Inc.*", filed Aug. 11, 2005.

Complaint, Amended, "*Abbott Diabetes Care, Inc. v. Dexcom, Inc.*", filed Jun. 27, 2006.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Csoregi, E., et al., "Design, Characterization, and One-Point in Vivo Calibration of a Subcutaneously Implanted Glucose Electrode", *Analytical Chemistry*, vol. 66 No. 19, 1994, pp. 3131-3138.

Csoregi, E., et al., "On-Line Glucose Monitoring by Using Microdialysis Sampling and Amperometric Detection Based on 'Wired' Glucose Oxidase in Carbon Paste", *Mikrochimica Acta*, vol. 121, 1995, pp. 31-40.

Dai, W. S., et al., "Hydrogel Membranes with Mesh Size Asymmetry Based on the Gradient Crosslinking of Poly(vinyl alcohol)," *Journal of Membrane Science*, vol. 156, 1999, pp. 67-79.

Davis, G., "Electrochemical Techniques for the Development of Amperometric Biosensors", *Biosensors*, vol. 1, 1985, pp. 161-178.

Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", *The Journal of Physical Chemistry*, vol. 91, No. 6, 1987, pp. 1285-1289.

Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", *Journal of the American Chemical Society*, vol. 110, No. 8, 1988, pp. 2615-2620.

Degani, Y., et al., "Electrical Communication Between Redox Centers of Glucose Oxidase and Electrodes via Electrostatically and Covalently Bound Redox Polymers", *Journal of the American Chemical Society*, vol. 111, 1989, pp. 2357-2358.

Denisevich, P., et al., "Unidirectional Current Flow and Charge State Trapping at Redox Polymer Interfaces on Bilayer Electrodes: Principles, Experimental Demonstration, and Theory", *Journal of the American Chemical Society*, vol. 103, 1981, pp. 4727-4737.

Dicks, J. M., et al., "Ferrocene Modified Polypyrrole with Immobilised Glucose Oxidase and its Application in Amperometric Glucose Microbiosensors", *Annales de Biologie Clinique*, vol. 47, 1989, pp. 607-619.

Ellis, C. D., et al., "Selectivity and Directed Charge Transfer through an Electroactive Metallopolymer Film", *Journal of the American Chemical Society*, vol. 103, No. 25, 1981, pp. 7480-7483.

Engstrom, R. C., "Electrochemical Pretreatment of Glassy Carbon Electrodes", *Analytical Chemistry*, vol. 54, No. 13, 1982, pp. 2310-2314.

Engstrom, R. C., et al., "Characterization of Electrochemically Pretreated Glassy Carbon Electrodes", *Analytical Chemistry*, vol. 56, No. 2, 1984, pp. 136-141.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Electron Transfer Kinetics at Redox Polymer/Solution Interfaces Using Microelectrodes and Twin Electrode Thin Layer Cells", *Journal of ElectroAnalytical Chemistry*, vol. 194, 1985, pp. 63-81.

Fischer, H., et al., "Intramolecular Electron Transfer Medicated by 4,4'-Bypyridine and Related Bridging Groups", *Journal of the American Chemical Society*, vol. 98, No. 18, 1976, pp. 5512-5517.

Flentge, F., et al., "An Enzyme-Reactor for Electrochemical Monitoring of Choline and Acetylcholine: Applications in High-Performance Liquid Chromatography, Bran Tissue, Microdialysis and Cerebrospinal Fluid," *Analytical Biochemistry*, vol. 204, 1992, pp. 305-310.

Foulds, N. C., et al., "Enzyme Entrapment in Electrically Conducting Polymers: Immobilisation of Glucose Oxidase in Polypyrrole and its Application in Amperometric Glucose Sensors", *Journal of the Chemical Society, Faraday Transactions 1*, vol. 82, 1986, pp. 1259-1264.

Foulds, N. C., et al , "Immobilization of Glucose Oxidase in Ferrocene-Modified Pyrrole Polymers", *Analytical Chemistry*, vol. 60, No. 22, 1988, pp. 2473-2478.

Frew, J. E., et al., "Electron-Transfer Biosensors", *Philosophical Transactions of the Royal Society of London*, vol. 316, 1987, pp. 95-106.

Godsland, I. F., et al., "Maximizing the Success Rate of Minimal Model Insulin Sensitivity Measurement in Humans: The Importance of Basal Glucose Levels," *Clinical Science*, Vol. 101, 2001, pp. 1-9.

Gorton, L., et al., "Selective Detection in Flow Analysis Based on the Combination of Immobilized Enzymes and Chemically Modified Electrodes", *Analytica Chimica Acta*, vol. 250, 1991, pp. 203-248.

Graham, N. B., "Poly(ethylene oxide) and Related Hydrogels," *Hydrogels in Medicine and Pharmacy, vol. II: Polymers, Chapter 4*, 1987, pp. 95-113.

Gregg, B. A., et al., "Cross-Linked Redox Gels Containing Glucose Oxidase for Amperometric Bionsensor Applications", *Analytical Chemistry*, vol. 62, No. 3, 1990, pp. 258-263.

Gregg, B. A., et al., "Redox Polymer Films Containing Enzymes. 1. A Redox-Conducting Epoxy Cement: Synthesis, Characterization, and Electrocatalytic Oxidation of Hydroquinone", *Journal of Physical Chemistry*, vol. 95, No. 15, 1991, 5970-5975.

Hale, P. D., et al., "A New Class of Amperometric Biosensor Incorporating a Polymeric Electron-Transfer Mediator", *Journal of the American Chemical Society*, vol. 111, No. 9, 1989, pp. 3482-3484.

Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.

Hawkridge, F. M., et al., "Indirect Coulometric Titration of Biological Electron Transport Components", *Analytical Chemistry*, vol. 45, No. 7, 1973, pp. 1021-1027.

Heller, A., "Electrical Connection Enzyme Redox Centers to Electrodes", *Journal of Physical Chemistry*, vol. 96, No. 9, 1990, pp. 3579-3587.

Heller, A., "Electrical Wiring of Redox Enzymes", *Accounts of Chemical Research* vol. 23, No. 5, 1990, 128-134.

Heller, A., et al., "Amperometric Biosensors Based on Three-Dimensional Hydrogel-Forming Epoxy Networks", *Sensors and Actuators B*, vol. 13-14, 1993, pp. 180-183.

Ianniello, R. M., et al., "Differential Pulse Voltammetric Study of Direct Electron Transfer in Glucose Oxidase Chemically Modified Graphite Electrodes", *Analytical Chemistry*, vol. 54, No. 7, 1982, pp. 1098-1101.

Ianniello, R. M., et al , "Immobilized Enzyme Chemically Modified Electrode as an Amperometric Sensor", *Analytical Chemistry*, vol. 53, No. 13, 1981, pp. 2090-2095.

Ikeda, T., et al., "Glucose Oxidase-Immobilized Benzoquinone-Carbon Paste Electrode as a Glucose Sensor", *Agricultural and Biological Chemistry*, vol. 49, No. 2, 1985, pp. 541-543.

Ikeda, T., et al., "Kinetics of Outer-Sphere Electron Transfers Between Metal Complexes in Solutions and Polymeric Films on Modified Electrodes", *Journal of the American Chemical Society*, vol. 103, No. 25, 1981, pp. 7422-7425.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, J. M., et al., "Potential-Dependent Enzymatic Activity in an Enzyme Thin-Layer Cell", *Analytical Chemistry*, vol. 54, No. 8, 1982, pp. 1377-1383.

Johnson, K. W., "Reproducible Electrodeposition of Biomolecules for the Fabrication of Miniature Electroenzymatic Biosensors", *Sensors and Actuators B*, vol. 5, 1991, pp. 85-89.

Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.

Johnson, P. C., "Peripheral Circulation", *John Wiley & Sons*, 1978, pp. 198.

Jonsson, G., et al., "An Amperometric Glucose Sensor Made by Modification of a Graphite Electrode Surface With Immobilized Glucose Oxidase and Adsorbed Mediator", *Biosensors*, vol. 1, 1985, pp. 355-368.

Josowicz, M., et al., "Electrochemical Pretreatment of Thin Film Platinum Electrodes", *Journal of the Electrochemical Society*, vol. 135 No. 1, 1988, pp. 112-115.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Katakis, I., et al., "Electrostatic Control of the Electron Transfer Enabling Binding of Recombinant Glucose Oxidase and Redox Polyelectrolytes", *Journal of the American Chemical Society*, vol. 116, No. 8, 1994, pp. 3617-3618.

Katakis, I., et al., "L-α-Glycerophosphate and L-Lactate Electrodes Based on the Electrochemical 'Wiring' of Oxidases", *Analytical Chemistry*, vol. 64, No. 9, 1992, pp. 1008-1013.

Kemp, G. J., "Theoretical Aspects of One-Point Calibration: Causes and Effects of Some Potential Errors, and Their Dependence on Concentration," *Clinical Chemistry*, vol. 30, No. 7, 1984, pp. 1163-1167.

Kenausis, G., et al., "'Wiring' of Glucose Oxidase and Lactate Oxidase Within a Hydrogel Made with Poly(vinyl pyridine) complexed with [Os(4,4'-dimethoxy-2,2'-bipyridine)2Cl]$^{+/2+}$", *Journal of the Chemical Society, Faraday Transactions*, vol. 92, No. 20, 1996, pp. 4131-4136.

Kerner, W., et al., "The Function of a Hydrogen Peroxide-Detecting Electroenzymatic Glucose Electrode is Markedly Impaired in Human Subcutaneous Tissue and Plasma," *Biosensors & Bioelectronics*, vol. 8, 1993, pp. 473-482.

Korf, J., et al., "Monitoring of Glucose and Lactate Using Microdialysis: Applications in Neonates and Rat Brain," *Developmental Neuroscience*, vol. 15, 1993, pp. 240-246.

Koudelka, M., et al., "In-Vivo Behaviour of Hypodermically Implanted Microfabricated Glucose Sensors", *Biosensors & Bioelectronics*, vol. 6, 1991, pp. 31-36.

Kulys, J., et al., "Mediatorless Peroxidase Electrode and Preparation of Bienzyme Sensors", *Bioelectrochemistry and Bioenergetics*, vol. 24, 1990, pp. 305-311.

Lager, W., et al., "Implantable Electrocatalytic Glucose Sensor", *Hormone Metabolic Research*, vol. 26, 1994, pp. 526-530.

Laurell, T., "A Continuous Glucose Monitoring System Based on Microdialysis", *Journal of Medical Engineering & Technology*, vol. 16, No. 5, 1992, pp. 187-193.

Lindner, E., et al., "Flexible (Kapton-Based) Microsensor Arrays of High Stability for Cardiovascular Applications", *Journal of the Chemical Society, Faraday Transactions*, vol. 89, No. 2, 1993, pp. 361-367.

Lortz, J., et al., "What is Bluetooth? We Explain The Newest Short-Range Connectivity Technology", *Smart Computing Learning Series, Wireless Computing*, vol. 8, Issue 5, 2002, pp. 72-74.

Maidan, R., et al., "Elimination of Electrooxidizable Interferant-Produced Currents in Amperometric Biosensors", *Analytical Chemistry*, vol. 64, No. 23, 1992, pp. 2889-2896.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

Marko-Varga, G., et al., "Enzyme-Based Biosensor as a Selective Detection Unit in Column Liquid Chromatography", *Journal of Chromatography A*, vol. 660, 1994, pp. 153-167.

Mastrototaro, J. J., et al., "An Electroenzymatic Glucose Sensor Fabricated on a Flexible Substrate", *Sensors and Actuators B*, vol. 5, 1991, pp. 139-144.

Mauras, N., et al., "Lack of Accuracy of Continuous Glucose Sensors in Healthy, Nondiabetic Children: Results of the Diabetes Research in Children Network (DirecNet) Accuracy Study," *Journal of Pediatrics*, 2004, pp. 770-775.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

McNeil, C. J., et al., "Thermostable Reduced Nicotinamide Adenine Dinucleotide Oxidase: Application to Amperometric Enzyme Assay", *Analytical Chemistry*, vol. 61, No. 1, 1989, pp. 25-29.

Miyawaki, O., et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, vol. 838, 1985, pp. 60-68.

Moatti-Sirat, D., et al., "Evaluating in Vitro and in Vivo the Interference of Ascorbate and Acetaminophen on Glucose Detection by a Needle-Type Glucose Sensor", *Biosensors & Bioelectronics*, vol. 7, 1992, pp. 345-352.

Moatti-Sirat, D., et al., "Reduction of Acetaminophen Interference in Glucose Sensors by a Composite Nafion Membrane: Demonstration in Rats and Man", *Diabetologia*, vol. 37, 1994, pp. 610-616.

Moatti-Sirat, D., et al., "Towards Continuous Glucose Monitoring: in Vivo Evaluation of a Miniaturized Glucose Sensor Implanted for Several Days in Rat Subcutaneous Tissue", *Diabetologia*, vol. 35, 1992, pp. 224-330.

Nagy, G., et al., "A New Type of Enzyme Electrode: The Ascorbic Acid Eliminator Electrode", *Life Sciences*, vol. 31, No. 23, 1982, pp. 2611-2616.

Nakamura, S., et al., "Effect of Periodate Oxidation on the Structure and Properties of Glucose Oxidase", *Biochimica et Biophysica Acta.*, vol. 445, 1976, pp. 294-308.

Narasimham, K., et al., "p-Benzoquinone Activation of Metal Oxide Electrodes for Attachment of Enzymes", *Enzyme and Microbial Technology*, vol. 7, 1985, pp. 283-286.

Ohara, T. J., "Osmium Bipyridyl Redox Polymers Used in Enzyme Electrodes", *Platinum Metals Review*, vol. 39, No. 2, 1995, pp. 54-62.

Ohara, T. J., et al., "'Wired' Enzyme Electrodes for Amperometric Determination of Glucose or Lactate in the Presence of Interfering Substances", *Analytical Chemistry*, vol. 66, No. 15, 1994, pp. 2451-2457.

Ohara, T. J., et al., "Glucose Electrodes Based on Cross-Linked [Os(bpy)$_2$Cl]$^{+/2+}$ Complexed Poly(1-Vinylimidazole) Films", *Analytical Chemistry*, vol. 65, No. 23, 1993, pp. 3512-3517.

Olievier, C. N., et al., "In Vivo Measurement of Carbon Dioxide Tension with a Miniature Electrodes", *Pflugers Archiv: European Journal of Physiology*, vol. 373, 1978, pp. 269-272.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", *Journal of ElectroAnalytical Chemistry*, vol. 260, 1989, pp. 487-494.

Palleschi, G., et al., "A Study of Interferences in Glucose Measurements in Blood by Hydrogen Peroxide Based Glucose Probes", *Analytical Biochemistry*, vol. 159, 1986, pp. 114-121.

Pankratov, I., et al., "Sol-Gel Derived Renewable-Surface Biosensors", *Journal of ElectroAnalytical Chemistry*, vol. 393, 1995, pp. 35-41.

Pathak, C., et al., "Rapid Photopolymerization of Immunoprotective Gels in Contact with Cells and Tissue", *Journal of the American Chemical Society*, vol. 114, No. 21, 1992, pp. 8311-8312.

Pickup, J., "Developing Glucose Sensors for in Vivo Use", *Tibtech*, vol. 11, 1993, pp. 285-291.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pickup, J., et al., "Potentially-Implantable, Amperometric Glucose Sensors with Mediated Electron Transfer: Improving the Operating Stability", *Biosensors*, vol. 4, 1989, pp. 109-119.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", *Diabetolgia*, vol. 36, 1993, pp. 658-663.

Poitout, V., et al., "Calibration in Dogs of a Subcutaneous Miniaturized Glucose Sensor Using a Glucose Meter for Blood Glucose Determination", *Biosensors & Bioelectronics*, vol. 7, 1992, pp. 587-592.

Poitout, V., et al., "In Vitro and in Vivo Evaluation in Dogs of a Miniaturized Glucose Sensor", *ASAIO Transactions*, vol. 37, No. 3, 1991, pp. M298-M300.

Pollak, A., et al., "Enzyme Immobilization by Condensation Copolymerization into Cross-Linked Polyacrylamide Gels", *Journal of the American Chemical Society*, vol. 102, No. 20, 1980, pp. 6324-6336.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Reach, G., et al., "Can Continuous Glucose Monitoring Be Used for the Treatment of Diabetes?", *Analytical Chemistry*, vol. 64, No. 6, 1992, pp. 381-386.

Rebrin, K., et al., "Automated Feedback Control of Subcutaneous Glucose Concentration in Diabetic Dogs", *Diabetologia*, vol. 32, 1989, pp. 573-576.

Reusch, W., "Other Topics: Organometallic Chemistry: Organometallic Compounds: Main Group Organometallic Compounds," *Virtual Textbook of Organic Chemistry*, 1999, Rev. 2007, 25 pages.

Roe, J. N., et al., "Bloodless Glucose Measurements", *Critical Review in Therapeutic Drug Carrier Systems*, vol. 15, Issue 3, 1998, pp. 199-241.

Sacks (ED), "Guidelines and Recommendations for Laboratory Analysis in the Diagnosis and Management of Diabetes Mellitus," *The National Academy of Clinical Biochemistry Presents Laboratory Medicine Practice Guidelines*, vol. 13, 2002, pp. 8-11, 21-23, 52-56, 63.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Samuels, G. J., et al., "An Electrode-Supported Oxidation Catalyst Based on Ruthenium (IV). pH 'Encapsulation' in a Polymer Film", *Journal of the American Chemical Society*, vol. 103, No. 2, 1981, pp. 307-312.

Sasso, S. V., et al., "Electropolymerized 1,2-Diaminobenzene as a Means to Prevent Interferences and Fouling and to Stabilize Immobilized Enzyme in Electrochemical Biosensors", *Analytical Chemistry*, vol. 62, No. 11, 1990, pp. 1111-1117.

Scheller, F. W., et al., "Second Generation Biosensors," *Biosensors & Bioelectronics*, vol. 6, 1991, pp. 245-253.

Scheller, F., et al., "Enzyme Electrodes and Their Application", *Philosophical Transactions of The Royal Society of London B*, vol. 316, 1987, pp. 85-94.

Schmehl, R. H., et al., "The Effect of Redox Site Concentration on the Rate of Mediated Oxidation of Solution Substrates by a Redox Copolymer Film", *Journal of ElectroAnalytical Chemistry*, vol. 152, 1983, pp. 97-109.

Schmidt, F. J., et al., "Calibration of a Wearable Glucose Sensor", *The International Journal of Artificial Organs*, vol. 15, No. 1, 1992, pp. 55-61.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems, Chapter 15*, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sittampalam, G., et al., "Surface-Modified Electrochemical Detector for Liquid Chromatography", *Analytical Chemistry*, vol. 55, No. 9, 1983, pp. 1608-1610.

Skoog, D. A., et al., "Evaluation of Analytical Data," *Fundamentals of Analytical Chemistry*, 1966, pp. 55.

Soegijoko, S., et al., "External Artificial Pancreas: A New Control Unit Using Microprocessor", *Hormone and Metabolic Research Supplement Series*, vol. 12, 1982, pp. 165-169.

Sprules, S. D., et al., "Evaluation of a New Disposable Screen-Printed Sensor Strip for the Measurement of NADH and Its Modification to Produce a Lactate Biosensor Employing Microliter Volumes", *Electroanalysis*, vol. 8, No. 6, 1996, pp. 539-543.

Sternberg, F., et al., "Calibration Problems of Subcutaneous Glucosensors when Applied 'In-Situ' in Man", *Hormone and Metabolic Research*, vol. 26, 1994, pp. 523-526.

Sternberg, R., et al., "Covalent Enzyme Coupling on Cellulose Acetate Membranes for Glucose Sensor Development", *Analytical Chemistry*, vol. 60, No. 24, 1988, pp. 2781-2786.

Sternberg, R., et al., "Study and Development of Multilayer Needle-Type Enzyme-Based Glucose Microsensors", *Biosensors*, vol. 4, 1988, pp. 27-40.

Suekane, M., "Immobilization of Glucose Isomerase", *Zettschrift fur Allgemeine Mikrobiologie*, vol. 22, No. 8, 1982, pp. 565-576.

Tajima, S., et al., "Simultaneous Determination of Glucose and 1,5-Anydroglucitol", *Chemical Abstracts*, vol. 111, No. 25, 1989, pp. 394.

Takamura, A., et al., Drug release from Poly(vinyl alcohol) Gel Prepared by Freeze-Thaw Procedure, *Journal of Controlled Release*, vol. 20, 1992, pp. 21-27.

Tarasevich, M. R., "Bioelectrocatalysis", *Comprehensive Treatise of Electrochemistry*, vol. 10, 1985, pp. 231-295.

Tatsuma, T., et al., "Enzyme Monolayer—and Bilayer-Modified Tin Oxide Electrodes for the Determination of Hydrogen Peroxide and Glucose", *Analytical Chemistry*, vol. 61, No. 21, 1989, pp. 2352-2355.

Taylor, C., et al., "'Wiring' of Glucose Oxidase Within a Hydrogel Made with Polyvinyl Imidazole Complexed with [(Os-4,4'-dimethoxy-2,2'-bipyridine)Cl]$^{+/2+}$", *Journal of ElectroAnalytical Chemistry*, vol. 396, 1995, pp. 511-515.

Thompson, M., et al., "In Vivo Probes: Problems and Perspectives", *Clinical Biochemistry*, vol. 19, 1986, pp. 255-261.

Trojanowicz, M., et al., "Enzyme Entrapped Polypyrrole Modified Electrode for Flow-Injection Determination of Glucose", *Biosensors & Bioelectronics*, vol. 5, 1990, pp. 149-156.

Tsalikian, E., et al., "Accuracy of the GlucoWatch G2® Biographer and the Continuous Glucose Monitoring System During Hypoglycemia: Experience of the Diabetes Research in Children Network", *Diabetes Care*, vol. 27, No. 3, 2004, pp. 722-726.

Turner, A., et al., "Diabetes Mellitus: Biosensors for Research and Management", *Biosensors*, vol. 1, 1985, pp. 85-115.

Turner, R. F., et al., "A Biocompatible Enzyme Electrode for Continuous in vivo Glucose Monitoring in Whole Blood", *Sensors and Actuators B*, vol. 1, 1990, pp. 561-564.

Tuzhi, P., et al., "Constant Potential Pretreatment of Carbon Fiber Electrodes for in Vivo Electrochemistry", *Analytical Letters*, vol. 24, No. 6, 1991, pp. 935-945.

U.S. Appl. No. 90/007,903, Request for Reexamination of U.S. Patent No. 6,565,509, filed Jan. 25, 2006.

U.S. Appl. No. 90/007,910, Request for Reexamination of U.S. Patent No. 6,175,752, filed Feb. 1, 2006.

U.S. Appl. No. 90/007,913, Request for Reexamination of U.S. Patent No. 6,284,478, filed Feb. 1, 2006.

U.S. Appl. No. 90/007,914, Request for Reexamination of U.S. Patent No. 6,329,161, filed Feb. 1, 2006.

U.S. Appl. No. 90/008,172, Request for Reexamination of U.S. Patent No. 6,990,366, filed Aug. 16, 2006.

U.S. Appl. No. 90/008,173, Request for Reexamination of U.S. Patent No. 6,134,461, filed Aug. 16, 2006.

U.S. Appl. No. 90/008,457, Request for Reexamination of U.S. Patent No. 6,990,366, filed Jan. 23, 2007.

U.S. Appl. No. 90/008,665, Request for Reexamination of U.S. Patent No. 6,284,478, filed May 25, 2007.

U.S. Appl. No. 90/008,713, Request for Reexamination of U.S. Patent No. 6,329,161, filed Jul. 25, 2007.

Umana, M., "Protein-Modified Electrochemically Active Biomaterial Surface", *U.S. Army Research Office, Analytical and Chemical Sciences Research Triangle Institute*, 1988, pp. 1-9.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring, Chapter 4*, 1997, pp. 117-137.

Urban, G., et al., "Miniaturized Thin-Film Biosensors Using Covalently Immobilized Glucose Oxidase", *Biosensors & Bioelectronics*, vol. 6, 1991, pp. 555-562.

Velho, G., et al., "In Vitro and in Vivo Stability of Electrode Potentials in Needle-Type Glucose Sensors", *Diabetes*, vol. 38, No. 2, 1989, pp. 164-171.

Velho, G., et al., "Strategies for Calibrating a Subcutaneous Glucose Sensor", *Biomedica Biochimica Acta*, vol. 48, 1989, pp. 957-964.

Von Woedtke, T., et al., "In Situ Calibration of Implanted Electrochemical Glucose Sensors", *Biomedica Biochimica Acta*, vol. 48, 1989, pp. 943-952.

Vreeke, M. S., et al., "Hydrogen Peroxide Electrodes Based on Electrical Connection of Redox Centers of Various Peroxidases to Electrodes through a Three-Dimensional Electron-Relaying Polymer Network", *Diagnostic Biosensors Polymers, Chapter 15*, 1993, pp. 180-193.

Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", *Analytical Chemistry*, vol. 64, No. 24, 1992, pp. 3084-3090.

Wang, D. L., et al., "Miniaturized Flexible Amperometric Lactate Probe", *Analytical Chemistry*, vol. 65, No. 8, 1993, pp. 1069-1073.

Wang, J., et al., "Activation of Glassy Carbon Electrodes by Alternating Current Electrochemical Treatment", *Analytica Chimica Acta*, vol. 167, 1985, pp. 325-334.

Wang, J., et al., "Amperometric Biosensing of Organic Peroxides with Peroxidase-Modified Electrodes", *Analytica Chimica Acta*, vol. 254, 1991, pp. 81-88.

Wang, J., et al., "Screen-Printable Sol-Gel Enzyme-Containing Carbon Inks", *Analytical Chemistry*, vol. 68, No. 15, 1996, pp. 2705-2708.

Wang, J., et al., "Sol-Gel-Derived Metal-Dispersed Carbon Composite Amperometric Biosensors", *Electroanalysis*, vol. 9, No. 1, 1997, pp. 52-55.

Williams, D. L., et al., "Electrochemical-Enzymatic Analysis of Blood Glucose and Lactate", *Analytical Chemistry*, vol. 42, No. 1, 1970, pp. 118-121.

Wilson, G. S., et al., "Progress Toward the Development of an Implantable Sensor for Glucose", *Clinical Chemistry*, vol. 38, No. 9, 1992, pp. 1613-1617.

Yabuki, S., et al., "Electro-Conductive Enzyme Membrane", *Journal of the Chemical Society, Chemical Communications*, 1989, pp. 945-946.

Yang, C., et al., "A Comparison of Physical Properties and Fuel Cell Performance of Nafion and Zirconium Phosphate/Nafion Composite Membranes," *Journal of Membrane Science*, vol. 237, 2004, pp. 145-161.

Yang, L., et al., "Determination of Oxidase Enzyme Substrates Using Cross-Flow Thin-Layer Amperometry", *Electroanalysis*, vol. 8, No. 8-9, 1996, pp. 716-721.

Yao, S. J., et al., "The Interference of Ascorbate and Urea in Low-Potential Electrochemical Glucose Sensing", *Proceedings of the Twelfth Annual International Conference of the IEEE Engineering in Medicine and Biology Science*, vol. 12, Part 2, 1990, pp. 487-489.

Yao, T., "A Chemically-Modified Enzyme Membrane Electrode as an Amperometric Glucose Sensor", *Analytica Chimica Acta*, vol. 148, 1983, pp. 27-33.

Ye, L., et al., "High Current Density 'Wired' Quinoprotein Glucose Dehydrogenase Electrode", *Analytical Chemistry*, vol. 65, No. 3, 1993, pp. 238-241.

Yildiz, A., et al., "Evaluation of an Improved Thin-Layer Electrode", *Analytical Chemistry*, vol. 40, No. 7, 1968, pp. 1018-1024.

Zamzow, K., et al., "New Wearable Continuous Blood Glucose Monitor (BGM) and Artificial Pancreas (AP)", *Diabetes*, vol. 39, 1990, pp. 5A-20.

Zhang, Y., et al., "Application of Cell Culture Toxicity Tests to the Development of Implantable Biosensors", *Biosensors & Bioelectronics*, vol. 6, 1991, pp. 653-661.

Zhang, Y., et al., "Elimination of the Acetaminophen Interference in an Implantable Glucose Sensor", *Analytical Chemistry*, vol. 66, No. 7, 1994, pp. 1183-1188.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Jungheim, K., et al., "How Rapid Does Glucose Concentration Change in Daily Life of Patients with Type 1 Diabetes?", 2002, pp. 250.

McGarraugh, G., et al., "Glucose Measurements Using Blood Extracted from the Forearm and the Finger", *TheraSense, Inc.*, 2001, 16 Pages.

Abstract for Japanese Patent Publication JP-55-010581 published Jan. 25, 1980.

Abstract for Japanese Patent Publication JP-55-010583 published Jan. 25, 1980.

Abstract for Japanese Patent Publication JP-55-010584 published Jan. 25, 1980.

* cited by examiner

METHOD AND SYSTEM FOR PROVIDING BASAL PROFILE MODIFICATION IN ANALYTE MONITORING AND MANAGEMENT SYSTEMS

BACKGROUND

The present invention relates to analyte monitoring systems and health management systems. More specifically, the present invention relates to method and system for providing basal profile modification in analyte monitoring systems to improve insulin therapy in diabetic patients.

In data communication systems such as continuous, semi-continuous or discrete analyte monitoring systems for insulin therapy, analyte levels of a patient are monitored and/or measured, and the measured analyte levels are used for treatment. For example, real time values of measured analyte levels of a patient would allow for a more robust and accurate diabetes treatment. Moreover, a profile of a series of measured analyte levels of a diabetic patient can provide valuable information regarding the fluctuations and variations of the analyte levels in a diabetic patient. In turn, this type of information would be invaluable in establishing a suitable insulin therapy regimen.

Many diabetic patients that use an infusion device such as an infusion pump generally have a preset or pre-established basal profiles which are programmed or stored into the infusion device by the patient's physician or the patient herself. Indeed, based on several factors such as insulin sensitivity, the patient's physiology and other variable factors that effect the patient's analyte levels, the physician may tailor the basal profiles of the patient to be programmed into the infusion device such that the patient's analyte level is maintained within an acceptable range, and thus the patient is not going to experience hyperglycemia or hypoglycemia.

While physicians attempt to best determine the most suitable basal profiles for each diabetic patient using the infusion device, it is often difficult to attain the most suitable profiles to ensure the safe operating range of the infusion device while providing the patient with the most suitable level of insulin at all times when the patient is wearing and operating the infusion device.

Often, diabetics who use infusion pumps run basal profiles to maintain a steady level of insulin and also, supplement with additional boluses administered typically with the same infusion pumps. Various devices exist that enable the determination of the appropriate bolus to supplement the basal profiles. For example, prior to the ingestion of a large quantity of carbohydrates, the patient is able to calculate a carbohydrate bolus and administer the same with the infusion pump so that the intake of the carbohydrates does not adversely impact the patient's physiology. While bolus supplements are useful and critical to a well managed insulin therapy regimen, it does not address the underlying concern related to the basal profiles that the infusion devices are programmed to administer.

In view of the foregoing, it would be desirable to have a method and system for providing basal profile modification for diabetic patients so as to comprehend each patient's unique physiology as well as response to insulin intake. More specifically, it would be desirable to modify basal profiles such that as the use of the infusion device progresses, the patient's basal profiles may be tailored to be more suitable for that patient

SUMMARY OF THE INVENTION

In accordance with the various embodiments of the present invention, there is provided a method and system for analyte monitoring and management configured to monitor the levels of a patient's analyte over a predetermined period of time, and based on the monitored analyte levels, determine one or more patterns in the analyte levels for the given period of time, and to provide a recommendation for modification to the basal profiles under which a medication delivery system such as an infusion pump is operating.

For example, in one embodiment, the analyte monitoring and management system of the present invention will be configured to monitor the analyte levels of a patient over a predetermined time period (for example, 1 day, 3 days, or 7 days), and during which, the patient is using an infusion device such as an insulin pump administering insulin based on a predetermined one or more basal profiles. Upon conclusion of the analyte level monitoring during the predetermined time period, the collected data are analyzed and, considered in conjunction with the underlying basal profiles under which the patient was infusing insulin during that same predetermined time period, used to determine a suitable modification to the basal profiles, if any, to improve the insulin therapy of the patient.

In this manner, a robust health management system may be provided which may be configured in one embodiment to monitor the analyte levels of a patient over a period of time and to recommend or suggest a modification to the existing or current basal profiles based on the collected and analyzed analyte levels taken in conjunction with the underlying basal profiles under which the infusion device was running during the time period of analyte level monitoring. Within the scope of the present invention, the monitored time period may vary depending upon the patient's need, the underlying basal profiles, the condition of the patient and the like, such that the patient may alter or modify the running basal profiles prior to its completion based on the monitored and analyzed analyte levels so as to provide a more effective insulin therapy.

DETAILED DESCRIPTION

Figure 1:
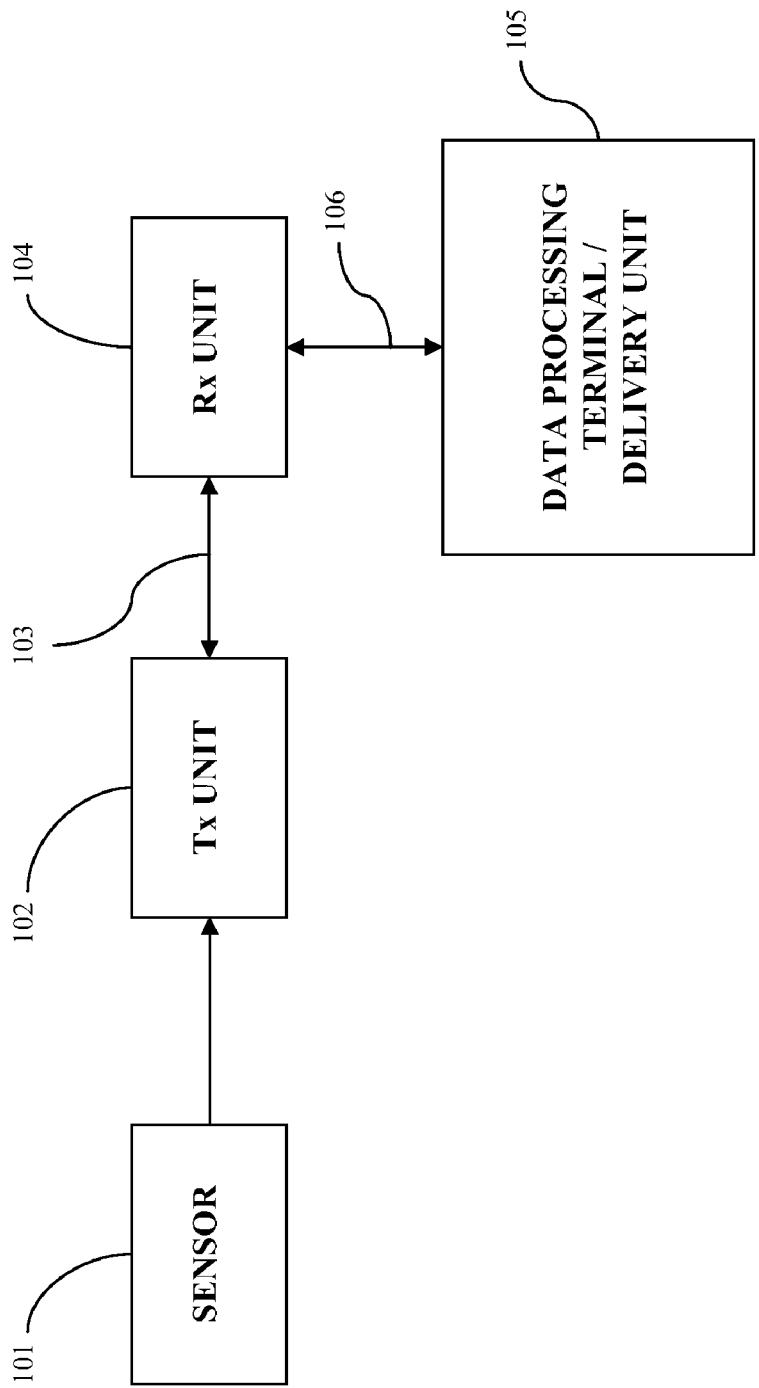
FIG. 1 illustrates a block diagram of a data monitoring and management system for practicing one embodiment of the present invention.

FIG. 1 illustrates a data monitoring and management system such as, for example, an analyte (e.g., glucose) monitoring and management system 100 in accordance with one embodiment of the present invention. The subject invention is further described primarily with respect to an analyte monitoring and management system for convenience and such description is in no way intended to limit the scope of the invention. It is to be understood that the analyte monitoring system may be configured to monitor a variety of analytes, e.g., lactate, and the like.

Indeed, analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

The analyte monitoring and management system 100 includes a sensor 101, a transmitter unit 102 coupled to the sensor 101, and a receiver unit 104 which is configured to communicate with the transmitter unit 102 via a communication link 103. The receiver unit 104 may be further configured to transmit data to a data processing terminal 105 for evaluating the data received by the receiver unit 104. Moreover, the data processing terminal in one embodiment may be configured to receive data directly from the transmitter unit 102 via a communication link 106 which may optionally be configured for bi-directional communication.

Only one sensor 101, transmitter unit 102, communication link 103, receiver unit 104, and data processing terminal 105 are shown in the embodiment of the analyte monitoring and management system 100 illustrated in FIG. 1. However, it will be appreciated by one of ordinary skill in the art that the analyte monitoring and management system 100 may include one or more sensor 101, transmitter unit 102, communication link 103, receiver unit 104, and data processing terminal 105, where each receiver unit 104 is uniquely synchronized with a respective transmitter unit 102. Moreover, within the scope of the present invention, the sensor 101 may include a subcutaneous analyte sensor, a transcutaneous analyte sensor, an implantable analyte sensor, or a noninvasive analyte sensor such as a transdermal patch or an optical sensor (for example, infrared sensor).

Moreover, within the scope of the present invention, the analyte monitoring system 100 may be a continuous monitoring system, or semi-continuous, or a discrete monitoring system. Additionally, within the scope of the present invention, the sensor 101 may include a subcutaneous analyte sensor or an implantable analyte sensor which is configured to be substantially wholly implanted in a patient.

In one embodiment of the present invention, the sensor 101 is physically positioned in or on the body of a user whose analyte level is being monitored. The sensor 101 may be configured to continuously sample the analyte level of the user and convert the sampled analyte level into a corresponding data signal for transmission by the transmitter unit 102. In one embodiment, the transmitter unit 102 is mounted on the sensor 101 so that both devices are positioned on the user's body. The transmitter unit 102 performs data processing such as filtering and encoding on data signals, each of which corresponds to a monitored analyte level of the user, for transmission to the receiver unit 104 via the communication link 103.

In one embodiment, the analyte monitoring system 100 is configured as a one-way RF communication path from the transmitter unit 102 to the receiver unit 104. In such embodiment, the transmitter unit 102 transmits the sampled data signals received from the sensor 101 without acknowledgement from the receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the receiver unit 104 may be configured to detect such transmitted encoded sampled data signals at predetermined time intervals. Alternatively, the analyte monitoring system 100 may be configured with a bi-directional RF (or otherwise) communication between the transmitter unit 102 and the receiver unit 104.

Additionally, in one aspect, the receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the receiver unit 104 is a data processing section which is configured to process the data signals received from the transmitter unit 102 such as by performing data decoding, error detection and correction, data clock generation, and data bit recovery.

In operation, upon completing the power-on procedure, the receiver unit 104 is configured to detect the presence of the transmitter unit 102 within its range based on, for example, the strength of the detected data signals received from the transmitter unit 102 or a predetermined transmitter identification information. Upon successful synchronization with the corresponding transmitter unit 102, the receiver unit 104 is configured to begin receiving from the transmitter unit 102 data signals corresponding to the user's detected analyte level. More specifically, the receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 in one embodiment may be configured to include a medication delivery unit such as an infusion device including, for example, an insulin pump, and which may be operatively coupled to the receiver unit 104. In such an embodiment, the medication delivery unit 105 may be configured to administer a predetermined or calculated insulin dosage based on the information received from the receiver unit 104. For example, as discussed in further detail below, the medication delivery unit 105 in one embodiment may be configured to deliver insulin based on pre-programmed basal profiles to diabetic patients, as well as to determine and/or administer one or more suitable bolus levels (e.g., carbohydrate bolus, and correction bolus).

Referring again to FIG. 1, the receiver unit 104 may include a personal computer, a portable computer such as a laptop or a handheld device (e.g., personal digital assistants (PDAs)), and the like, each of which may be configured for data communication with the receiver via a wired or a wireless connection. Additionally, the receiver unit 104 may further be connected to a data network (not shown) for storing, retrieving and updating data corresponding to the monitored analyte levels of the patient.

Furthermore, in one embodiment of the present invention, the receiver unit 104 or the data processing terminal 105, or both the receiver unit 104 and the data processing terminal 105 may be configured to incorporate a glucose strip meter so as to be configured to include, for example, a test strip port for receiving a glucose test strip. In this embodiment of the present invention, the receiver unit 104 and the data processing terminal 105 may be configured to perform analysis upon the sample from the glucose test strip so as to determine the glucose level from the test strip. One example of such strip meter is Freestyle® glucose meters commercially available from the assignee of the present invention, Abbott Diabetes Care Inc. of Alameda Calif.

Furthermore, within the scope of the present invention, the data processing terminal 105 may include an infusion device such as an insulin infusion pump or the like, which may be configured to administer insulin to patients, and which may be configured to communicate with the receiver unit 104 for receiving, among others, the measured glucose level. Alternatively, the receiver unit 104 may be configured to integrate an infusion device therein so that the receiver unit 104 is configured to administer insulin therapy to patients, for example, for administering and modifying basal profiles, as well as for determining appropriate boluses for administration based on, among others, the detected analyte levels received from the transmitter unit 102.

Additionally, the transmitter unit 102, the receiver unit 104 and the data processing terminal 105 may each be configured for bi-directional wireless communication such that each of the transmitter unit 102, the receiver unit 104 and the data processing terminal 105 may be configured to communicate (that is, transmit data to and receive data from) with each other via the wireless communication link 103. More specifically, the data processing terminal 105 may in one embodiment be configured to receive data directly from the transmitter unit 102 via the communication link 106, where the communication link 106, as described above, may be configured for bi-directional communication. In this embodiment, the data processing terminal 105 which may include an insulin pump, may be configured to receive the analyte signals from the transmitter unit 102, and thus, incorporate the functions of the receiver 104 including data processing for managing the patient's insulin therapy and analyte monitoring.

In one embodiment, the communication link 103 may include one or more of an RF communication protocol, an infrared communication protocol, a Bluetooth® enabled communication protocol, an 802.11x wireless communication protocol, or an equivalent wireless communication protocol which would allow secure, wireless communication of several units (for example, per HIPPA requirements) while avoiding potential data collision and interference.

Figure 2:
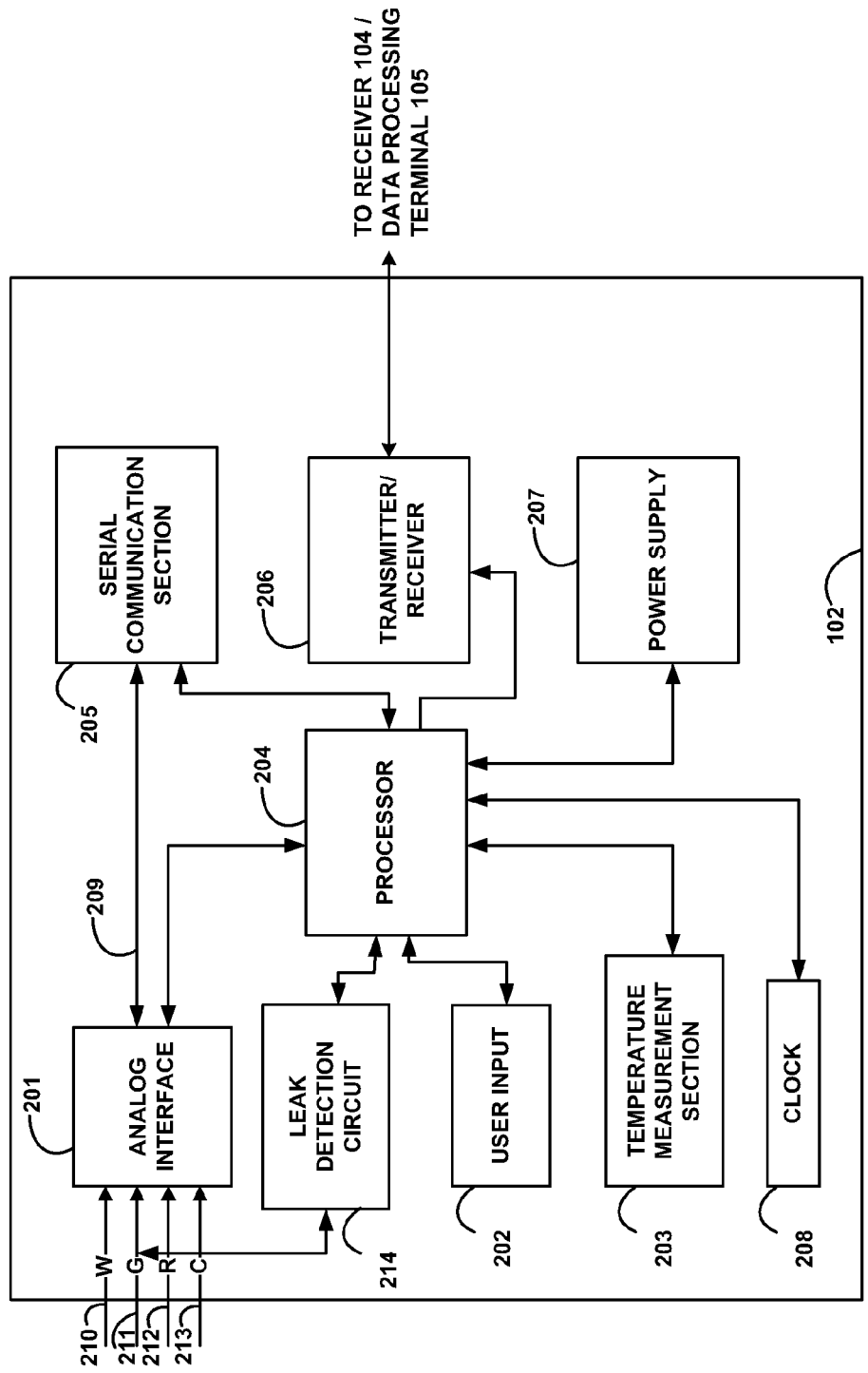
FIG. 2 is a block diagram of the transmitter unit of the data monitoring and management system shown in FIG. 1 in accordance with one embodiment of the present invention.

FIG. 2 is a block diagram of the transmitter of the data monitoring and detection system shown in FIG. 1 in accordance with one embodiment of the present invention. Referring to the Figure, the transmitter 102 in one embodiment includes an analog interface 201 configured to communicate with the sensor 101 (FIG. 1), a user input 202, and a temperature measurement section 203, each of which is operatively coupled to a transmitter processor 204 such as a central processing unit (CPU). As can be seen from FIG. 2, there are provided four contacts, three of which are electrodes—work electrode (W) 210, guard contact (G) 211, reference electrode (R) 212, and counter electrode (C) 213, each operatively coupled to the analog interface 201 of the transmitter 102 for connection to the sensor unit 101 (FIG. 1). In one embodiment, each of the work electrode (W) 210, guard contact (G) 211, reference electrode (R) 212, and counter electrode (C) 213 may be made using a conductive material that is either printed or etched, for example, such as carbon which may be printed, or metal foil (e.g., gold) which may be etched.

Further shown in FIG. 2 are a transmitter serial communication section 205 and an RF transmitter 206, each of which is also operatively coupled to the transmitter processor 204. Moreover, a power supply 207 such as a battery is also provided in the transmitter 102 to provide the necessary power for the transmitter 102. Additionally, as can be seen from the Figure, clock 208 is provided to, among others, supply real time information to the transmitter processor 204.

In one embodiment, a unidirectional input path is established from the sensor 101 (FIG. 1) and/or manufacturing and testing equipment to the analog interface 201 of the transmitter 102, while a unidirectional output is established from the output of the RF transmitter 206 of the transmitter 102 for transmission to the receiver 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter 102 is configured to transmit to the receiver 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter 102 for operation upon completion of the manufacturing process as well as for direct communication for diagnostic and testing purposes.

As discussed above, the transmitter processor 204 is configured to transmit control signals to the various sections of the transmitter 102 during the operation of the transmitter 102. In one embodiment, the transmitter processor 204 also includes a memory (not shown) for storing data such as the identification information for the transmitter 102, as well as the data signals received from the sensor 101. The stored information may be retrieved and processed for transmission to the receiver 104 under the control of the transmitter processor 204. Furthermore, the power supply 207 may include a commercially available battery.

The transmitter 102 is also configured such that the power supply section 207 is capable of providing power to the transmitter for a minimum of about three months of continuous operation after having been stored for about eighteen months in a low-power (non-operating) mode. In one embodiment, this may be achieved by the transmitter processor 204 operating in low power modes in the non-operating state, for example, drawing no more than approximately 1 µA of current. Indeed, in one embodiment, the final step during the manufacturing process of the transmitter 102 may place the transmitter 102 in the lower power, non-operating state (i.e., post-manufacture sleep mode). In this manner, the shelf life of the transmitter 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present invention, the power supply unit 207 is configured to provide the necessary power to each of the components of the transmitter unit 102 shown in FIG. 2.

Referring back to FIG. 2, the power supply section 207 of the transmitter 102 in one embodiment may include a rechargeable battery unit that may be recharged by a separate power supply recharging unit so that the transmitter 102 may be powered for a longer period of usage time. Moreover, in one embodiment, the transmitter 102 may be configured without a battery in the power supply section 207, in which case the transmitter 102 may be configured to receive power from an external power supply source (for example, a battery) as discussed in further detail below.

Referring yet again to FIG. 2, the temperature measurement section 203 of the transmitter 102 is configured to monitor the temperature of the skin near the sensor insertion site. The temperature reading is used to adjust the analyte readings obtained from the analog interface 201. The RF transmitter 206 of the transmitter 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the receiver 104.

Referring yet again to FIG. 2, also shown is a leak detection circuit 214 coupled to the guard electrode (G) 211 and the processor 204 in the transmitter 102 of the data monitoring and management system 100. The leak detection circuit 214 in accordance with one embodiment of the present invention may be configured to detect leakage current in the sensor 101 to determine whether the measured sensor data are corrupt or whether the measured data from the sensor 101 is accurate.

Additional detailed description of the continuous analyte monitoring system, its various components including the functional descriptions of the transmitter are provided in U.S. Pat. No. 6,175,752 issued Jan. 16, 2001 entitled "Analyte Monitoring Device and Methods of Use", and in application Ser. No. 10/745,878 filed Dec. 26, 2003 entitled "Continuous Glucose Monitoring System and Methods of Use", each assigned to the Assignee of the present application, and the disclosures of each of which are incorporated herein by reference for all purposes.

Figure 3:
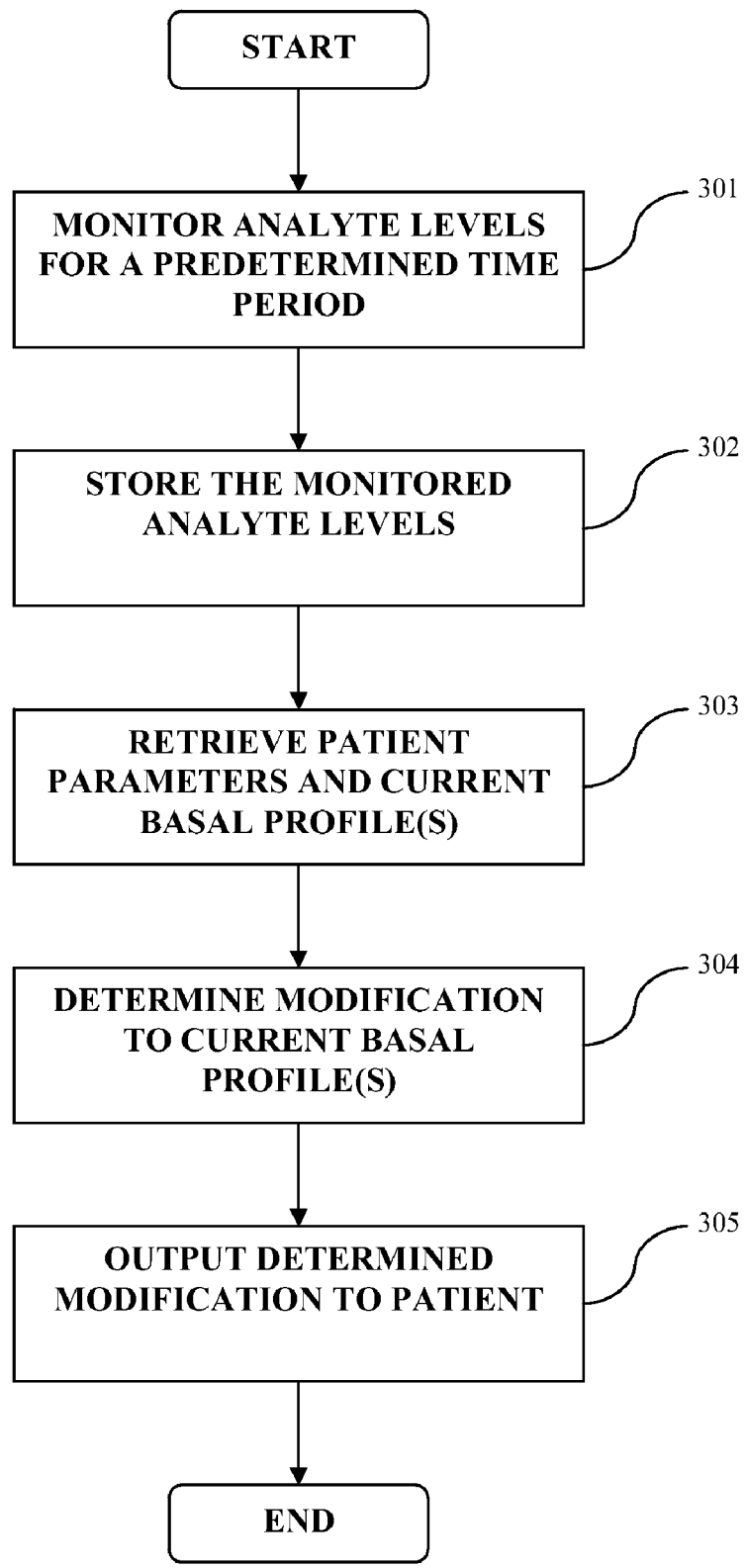
FIG. 3 is a flowchart illustrating the process for monitoring analyte levels and determining modification to a current basal profile in accordance with one embodiment of the present invention.

FIG. 3 is a flowchart illustrating the process for monitoring analyte levels and determining modification to a current basal profile in accordance with one embodiment of the present invention. Referring to FIG. 3, at step 301, the analyte levels such as the patient's analyte level is monitored for a predetermined period of time, and at step 302, the monitored analyte levels is stored in a data storage unit (for example, in one or more memory devices of the receiver unit 104 and/or the data processing terminal 105 (FIG. 1)). Thereafter, at step 303, patient specific parameters are retrieved from the data processing terminal 105 and/or the receiver unit 104, as well as the current basal profile(s) which the patient is implementing to operate the infusion device for insulin delivery during the time period of the analyte monitoring discussed above.

In one embodiment, patient specific parameters may include the type of insulin currently being infused into the patient, the patient's insulin sensitivity, insulin resistance level, level of insulin on board, the specific time period of the analyte monitoring, including the activities performed by the patient during that time period, or any other factors and variables that may have an impact upon the effectiveness of insulin therapy for the patient.

Referring to FIG. 3, after retrieving the patient specific parameters and the current basal profile(s) that the patient is implementing in the infusion device at step 303, at step 304, the monitored analyte levels are retrieved and, based on one or more patterns from the analyte levels monitored and factoring in the current basal profile(s), a recommendation or modification to the current basal profile(s) is determined. Thereafter, the recommendation or modification to the current basal profiles(s) determined at step 304 is provided to the patient visually on a display or audibly, or a combination of visual and audio output, such that the patient may be able to decide whether the modification to the current basal profile(s) is appropriate or suitable to the patient.

While the modification to the basal profile(s) is discussed above as output to the patient, within the scope of the present invention, the basal profile modification determined in accordance with one embodiment of the present invention may be provided to a health care provider so as to determine suitability of the modification to the current basal profile in view of the monitored analyte levels. Furthermore, in an alternate embodiment, the determined modification to the current basal profile may be provided to both the patient and the health care provider so that the patient is able to make an informed decision as to whether the recommended modification to the current basal profile is suitable for the patient in improving insulin therapy to better manage diabetes.

Within the scope of the present invention, the modification to the current basal profile may include several factors that are considered including, for example, the current basal profile as a function of the time period during which insulin infusion takes place and analyte levels are monitored, the level of the analyte monitored as a function of time, patient specific parameters discussed above including, for example, patient's activities during the monitored time period, patient's diet, insulin sensitivity, level of insulin on board, and the insulin type, and the frequency of bolus dosing during the time period of the analyte level monitoring (for example, the number of correction bolus dosing, and/or carbohydrate dosing).

In this manner, in one embodiment of the present invention, the modification to the current basal profile(s) may be achieved for one or more specific goals for the patient's diabetes management, including for example, elimination of extreme glucose excursions, automating or semi-automating routine or regular bolus dosing, and adjustment to the mean glucose value.

For example, to effectively eliminate extreme glucose excursions, the modification to the current basal profiles may be configured to provide recommendation to modify to reduce extreme levels, so that unless the monitored glucose level exceeds a predetermined threshold level (e.g., 200 mg/dL), modification to the current basal profile is not recommended. In the case of automating regular bolus dosing, based on the monitored analyte levels, a regular correction bolus dosing during the current basal profile implementation may be converted into a modification to the current basal profile so that the patient may effectively be rid of the need to implement routine correction type bolus dosing. Additionally, with the collected data from the continuously monitored analyte levels, the current basal profile may be modified to adjust the mean target glucose value even in the case where extreme excursions of glucose levels do not occur.

Within the scope of the present invention, the current basal profile modification may be performed at different times during the time that the patient is using an infusion device. For example, the patient may perform the current basal profile modification procedure discussed above on a daily basis if, for example, glucose excursions are anticipated on a regular basis. Alternatively, the current basal profile modification procedure may be performed each time a bolus is administered.

Moreover, within the scope of the present invention, when a pattern of glucose excursions is detected over several days (for example, 48 or 72 hours), the analyte monitoring and management system 100 (FIG. 1) may be configured to continue analyte level monitoring to determine whether a pattern exists in the frequency and/or level of the glucose excursions. In such a case, it is possible to modify the current basal profile modification procedure to correct for such patterns in the monitored analyte levels such that the modification to the current basal profile may address such excursions.

In a further embodiment, the loop gain setting may be configured to determine the appropriate level of modification to the current basal profiles for a given glucose excursion pattern detected based on the monitored analyte levels. While several iterations may be necessary for low loop gain to reach the optimal modification level of the current basal profile, a conservative and less aggressive modification may be recommended in such cases. For medium loop gain, when critically controlled, the determined recommendation for modification to the current basal profile may be reached based on one iteration, but with the potential for an increased risk for overshoot and thereby resulting in over-compensation. Notwithstanding, the loop gain setting may be trained into the analyte monitoring and management system 100 so that by starting with a low loop gain and then learning the loop responses to reach the optimal loop gain, the desired modification to the current basal profile may be determined and provided to the patient.

Figure 4A:
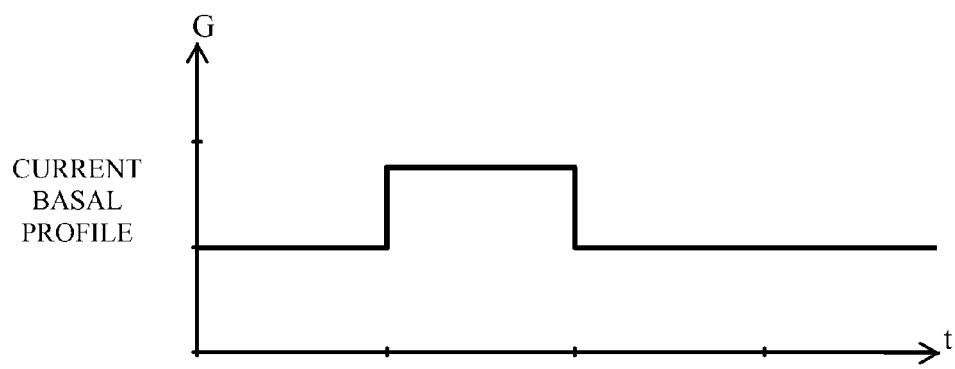
FIGS. 4A-4C illustrate a current basal profile, a monitored analyte level profile, and a modified basal profile recommendation respectively, in accordance with one embodiment of the present invention.
Figure 4B:
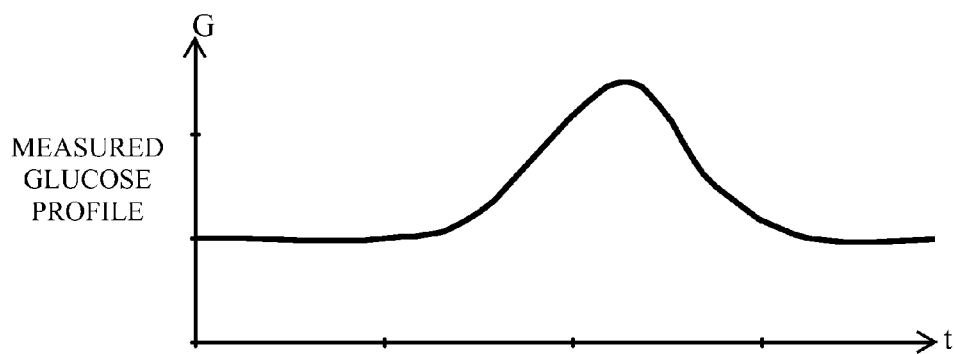
Figure 4C:
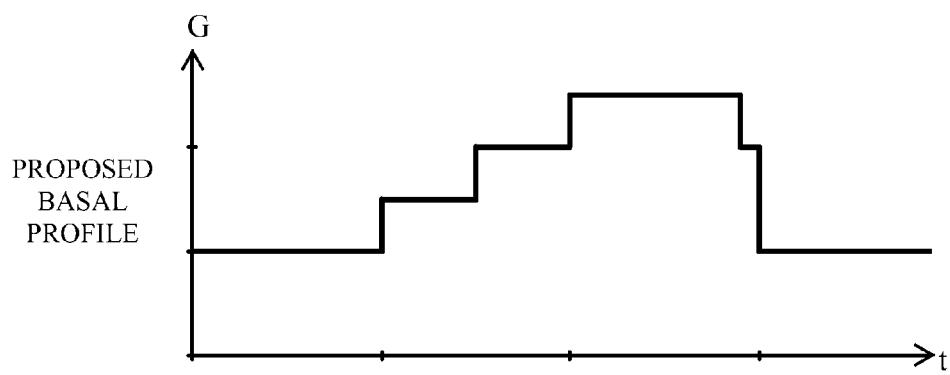

FIGS. 4A-4C illustrate a current basal profile, a monitored analyte level profile, and a modified basal profile recommendation respectively, in accordance with one embodiment of the present invention. Referring to FIG. 4A, a profile of the glucose level as a function of time is shown for a current basal profile programmed into the infusion device of the patient. FIG. 4B illustrates a profile of the glucose levels as a function of time for the same time period during which the basal profile shown in FIG. 4A is administered to the patient. Finally, FIG. 4C illustrates a profile of glucose level as a function of time which factors in the patient parameters including the monitored glucose levels of the patient, to provide a modification to the current basal profile so as to improve the patient's insulin therapy.

Indeed, in one embodiment of the present invention, it can be seen that the analyte level monitoring and detecting patterns in the monitored analyte levels during the time period that the patient is using an infusion device such as an insulin pump running a pre-programmed basal profile, provides contemporaneous patient response of the infused insulin based on the current basal profile, and thus, it is possible to improve the insulin therapy.

By way of an example, in the case that the patient desired to eliminate or substantially reduce the occurrences of high glucose extremes or excursions, it is determined whether there is a consistent pattern of high glucose levels versus time of day of such occurrence based on the monitored glucose levels. An example of such monitored levels is shown in the Table 1 below:

TABLE 1

High Glucose Excursions

|  | 00:00 | 00:30 | 01:00 | 01:30 | 23:30 |
|---|---|---|---|---|---|
| Day 1 (0-24 hr) |  |  | 1 | 1 |  |
| Day 2 (24-48 hr) | 1 |  | 1 | 1 |  |
| Day 3 (48-72 hr) | 1 | 1 | 1 | — | — |
| Sum | 2 | 1 | 3 | 2 | 0 | where over a 72 hour period post calibration of the sensor 101 (FIG. 1), the monitored data is reviewed to determine if the monitored glucose level exceeds a predetermined threshold level. Each occurrence of when the glucose level exceeds a predetermined threshold level is shown with a "1" in Table 1 above.

For each column shown in Table 1 where the sum of the data entry equals "3", and the sum of the adjacent columns is equal to or greater than "1", the analyte monitoring and management system 100 in one embodiment may be configured to recommend an increase to the current basal profile for that time slot or period during the 72 hour period.

More specifically, using a conventional bolus calculation mechanism, a correction bolus may be determined based on the detection of the high glucose level. Thereafter, rather than implementing the calculated correction bolus, the modification to the current basal profile may be determined based on the following relationship:

$$\text{Modification} = K * \text{Calculated Correction Bolus}/30 \text{ minutes} \quad (1)$$

where K is a loop gain value determined by the patient's health care provider, and is typically less than 1 for over dampened control, and further, where the 30 minutes is a scaling factor for the Modification determination.

After the calculation, the determined Modification from the equation (1) above is provided to the patient to either accept and implement, storage for further analysis or modification, or reject.

In one embodiment, the Modification determination based on relationship described in the equation (1) above may include glucose rate or higher derivative information, or alternatively, may also include an integral factor. In a further embodiment, the determination may also factor in the glucose profile variation. Other potentially relevant factors also include the physiological dynamics and/or sensor/monitor dynamics, as well as the patient's insulin infusions, caloric intake, exercise, etc.

As another example, in the case where correction bolus dosing may be replaced with modification to the current basal profiles based on the monitored analyte levels, a consistent pattern in the monitored analyte levels of bolus delivery versus time of day is determined. Table 2 below shows one example of such pattern:

TABLE 2

Bolus Replacement

|  | 00:00 | 00:30 | 01:00 | 01:30 | 23:30 |
|---|---|---|---|---|---|
| Day 1 (0-24 hr) |  |  | 1 | 1 |  |
| Day 2 (24-48 hr) | 1 |  | 1 | 1 |  |
| Day 3 (48-72 hr) | 1 | 1 | 1 | — | — |
| Sum | 2 | 1 | 3 | 2 | 0 |

Referring to Table 2 and in conjunction with equation (1) discussed above, the administration of bolus doses is reviewed and if, for example, there were three bolus deliveries (each shown in Table 2 with a "1" entry) within 30 minutes of the same time of day period, then an increase in the insulin level for same time period may be proposed to the current basal profile using equation (1) to determine the level of modification to the current basal profile.

In the case of addressing the occurrence of low extremes of glucose levels, similar determinations as above may be performed given the monitored analyte levels for the desired time period and data reviewed for detection of patterns in the monitored analyte levels associated with the occurrences of low extremes. For example, Table 3 below provides data for a three day period illustrating patterns associated with the occurrences of low extremes.

TABLE 3

Low Extremes Pattern

|  | 00:00 | 00:30 | 01:00 | 01:30 | 23:30 |
|---|---|---|---|---|---|
| Day 1 (0-24 hr) |  |  | 1 | 1 |  |
| Day 2 (24-48 hr) | 1 |  | 1 | 1 |  |
| Day 3 (48-72 hr) | 1 | 1 | 1 | — | — |
| Sum | 2 | 1 | 3 | 2 | 0 | where the "1" entry in a particular column illustrates the occurrence of the measured glucose level that is below a predetermined low threshold level.

Again, in conjunction with equation (1) above, a modification to the current basal profile may be determined and provided to the patient. More specifically, where over a 72 hour period post calibration of the sensor 101 (FIG. 1), the monitored data is reviewed to determine if the monitored glucose level falls below the predetermined low threshold level, each such is shown with a "1" in Table 3 above.

For each column shown in Table 3 where the sum of the data entry equals "3", and the sum of the adjacent columns is equal to or greater than "1", the analyte monitoring and management system 100 in one embodiment may be configured to recommend a modification to the current basal profile for that time slot or period during the 72 hour period based on the relationship set forth in equation (1). The user or patient may then be provided with the modification to the current basal profile which may be accepted for implementation, stored for further analysis or modification, or rejected by the patient.

In the case of reducing the mean glucose level using the analyte monitoring and management system 100 in one embodiment of the present invention, again, consistent patterns in the monitored analyte levels over a predetermined time period is analyzed and detected as a function of time of day of the analyte level monitoring. Table 4 below shows an example of such pattern:

TABLE 4

| | Mean Glucose Level | | | | |
|---|---|---|---|---|---|
| | 00:00 | 00:30 | 01:00 | 01:30 | 23:30 |
| Day 1 (0-24 hr) | | | 1 | 1 | |
| Day 2 (24-48 hr) | 1 | | 1 | 1 | |
| Day 3 (48-72 hr) | 1 | 1 | 1 | | |
| Sum | 2 | 1 | 3 | 2 | 0 | where, an entry of a "1" in Table 4 above illustrates a detected glucose level of greater than a predetermined level (e.g., 120) during the three day period based on the data from the sensor 101 (FIG. 1).

Again, similar to the determinations above, if the sum of any column in Table 4 is equal to three, and the sum of the adjacent columns is greater than or equal to one, then a decrease in the current basal profile for that particular time slot is recommended based on the relationship set forth above in equation (1).

In a further embodiment, a 24 hour profile may be determined based on time-of-day averages over a predetermined number of days. The correction factor may then be based on maintaining the time-of-day averages within a predetermined target range value. Within the scope of the present invention, the various approaches and implementations for correction calculation and/or basal profile modification recommendation may be combined or implemented individually, depending upon the patient's physiology and the criteria for drug therapy such as insulin therapy.

In accordance with the various embodiments of the present invention, additional or alternative approaches to the determination of the modification to the basal profile may include, for example, (1) modifying the basal rate by a constant value, (2) changing the basal rate by a constant percentage of the current basal profile rate, (3) changing the basal rate in proportion to the magnitude of the error, or (4) changing the basal rate in proportion to the magnitude of the error, compensating for the loop gain factor based on the affects of the previous basal rate modifications/adjustments. Each of these approaches within the scope of the present invention is described in further detail below.

In the first embodiment described above, the basal rate is configured for modification by a constant amount. For example, the modification is described by the following equation (2):

$$\text{Modification} = \text{sign(measured−target)} * U \quad (2)$$

where U is a constant value in insulin units, and is applied to the difference between the target glucose and measured glucose levels.

Moreover, the "sign(measured−target)" relationship holds the following:
if(measured−target)=0, then 0
else if (measured−target)>0, then +1
else if (measured−target)<0, then −1

For example, in the equation (2) above, the constant value U may be 0.1 units of insulin/hour. This may be a configurable value. Indeed, for the case where U is 0.1 units, if the measured glucose level is 140, while the target glucose level is 100, then the Modification to the basal rate would result in +1*0.1 equaling 0.1 units/hour.

In this manner, in one embodiment, a simple and effective basal rate modification approach is provided and which does not require knowledge of the patient's physiology, is simple to implement, and does not provide resolution issues. On the other hand, for safely values of the constant factor U, several iterations or corrections may be needed to reach the desired results.

In another embodiment, the basal rate may be modified by a constant percentage of the current rate. In this case, the following equation (3) holds:

$$\text{Modification} = \text{sign(measured−target)} * K * U \quad (3)$$

where K=constant percentage, $0 \leq K \leq 1$, and U=current basal rate (in units of insulin).

For example, where the constant percentage K is 0.1 and with the current basal rate U of 2.0 units/hour, and for example, the measured and target glucose levels at 140 and 100, respectively, the basal rate Modification in accordance with the equation (3) equals +1*0.1*2.0=0.2 units/hour. In this manner, in one embodiment, a simple and effective way to implement basal rate modification is provided, and which does not require the knowledge of the user's physiology. For safe values of the constant percentage K, several iterations may be needed to reach the desired level of basal rate modification, and resolution issues may potentially arise.

In a further embodiment of the present invention, the modification to the basal rate may be determined by changing the basal rate proportional to the magnitude of the error. In this case, the following equation (4) holds:

$$\text{Modification} = \text{(measured−target)} * K * P \quad (4)$$

where K is the loop gain factor, and for example, K<1 for dampened control, K=1 for critical control, K>1 for over control, and further, where P is the patient's physiological response to insulin (insulin sensitivity).

For example, in the case where the loop gain factor K is 0.75, the patient's insulin sensitivity P is 0.02 units/mg/dL, and where the measured and target glucose levels are 140 and 100, respectively, the Modification to the basal rate in accordance to equation (4) is determined to be (140−100)*0.75*0.02=0.6 units/hour. This approach requires prior determination of the patient's insulin sensitivity, and may likely require less iterations or corrective routines to reach the desired level of basal rate modification for effective treatment.

In still a further embodiment, the modification to the basal rate may be determined by the changing the basal rate proportional to the magnitude of error, and further making adjustment to the loop gain factor based on the results of the prior basal rate adjustments. For example, the following equation (5) holds:

with K=f(affect of last adjustment)

$$\text{Modification}=(\text{measured}-\text{target})*K*P \quad (5)$$

where K is loop gain factor, and P is the patient's physiology response to insulin (insulin sensitivity).

For example, if the loop gain factor is initially 0.75, then the determined basal rate modification is the same as in the embodiment described above in conjunction with equation (4). In the next iteration, with the measured glucose level still higher than the target level, the look gain factor is increased. In this case, for example, with measured glucose level of 110 where the target level is 100, the new loop gain factor K is determined to be ((first delta)/(first change))*old K=(40/30) *0.75=1.00.

Having determined the new loop gain factor K, the basal rate modification is determined by equation (5) as (110-100) *1.00*0.02=0.2 units/hour. It is to be noted that if the loop gain factor K did not change between the two iterations described above, then the basal rate modification in the second iteration may be relatively smaller, and it can be seen that the adjustment to the loop gain factor allows faster settling to the final value. For example, using equation (5) above, the basal rate modification is determined as:

$$\text{Modification}=(110-100)*0.75*0.02=0.15 \text{ units/hour}$$

In this manner, in one embodiment of the present invention, the basal rate modification may be configured to self adjust to the patient's physiology such that it may be more tolerant of inaccurate input values.

In this manner, the various embodiments of the present invention provides a mechanism for diabetic patients to compare the actual glucose levels during a predetermined time period and to use that information in addition to the actual basal profile to recommend a new or modified basal profile to the patient. The patient will have the option to accept the recommendation, the accept the recommendation with the modification, or alternatively to decline the proposed modified basal profile so as to select the most appropriate basal profile for the patient.

Moreover, contrasting with real time closed loop insulin therapy where the insulin infusion is modified at a rate (i.e., minutes) much faster than the physiological response times, one embodiment of the present invention is characterized by a) corrections to basal profiles that are made over periods (i.e., days) which are much longer than physiological response times, and b) corrections based on repeating diurnal glucose patterns. In this manner, in one embodiment, the present invention is configured to identify the patient's glucose levels retrospectively over a predetermined period of time (for example, over a 24 hour period) to determine any recommended modification to the existing basal profiles. In this manner, the recommended modification to the basal profiles will be a function of the actual measured glucose values of the patient under the existing basal profiles.

In the manner described above, in accordance with the various embodiments of the present invention, the patient and the doctor or educator may work together to adjust the insulin profile to the patient's activities. This will require experience and some trial and error as well. An automated basal profile correction in accordance with the embodiments of the present invention may monitor and gather much more information and may incorporate the knowledge of the physician/educator within the modification algorithm. Indeed, different objectives can be identified and the modification algorithms developed to achieve the objectives.

Accordingly, a method in one embodiment includes monitoring an analyte level of a patient, retrieving a predetermined parameter, and determining a modification to an drug therapy profile based on the monitored analyte level and the predetermined parameter.

The analyte includes glucose, and the drug infusion rate may include a basal profile.

Further, the predetermined parameter may include one or more of an insulin sensitivity, a drug infusion rate, and a drug infusion time period, a time period corresponding to the monitored analyte level, a time of day associated with the monitored analyte level, or a loop gain factor.

Moreover, the monitoring step may include determining the analyte level of the patient at a predetermined time interval including one of 5 minutes, 30 minutes, 1 hour, or 2 hours.

The method in one embodiment may further include the step of outputting the modification to the drug therapy profile to the patient.

Also, the method may additionally include the step of implementing the modification to the drug therapy profile.

In a further aspect, the drug therapy profile may include an insulin infusion profile.

A system in yet another embodiment of the present invention includes an analyte monitoring unit, and a processing unit operatively coupled to the analyte monitoring unit, the processing unit configured to receive a plurality of monitored analyte levels of a patient, and to determine a modification to a drug therapy profile based on the received plurality of monitored analyte levels.

The analyte monitoring unit in one embodiment may include a sensor unit provided in fluid contact with an analyte of a patient.

Further, the sensor unit may include a subcutaneous analyte sensor, a transcutaneous analyte sensor, and a transdermal patch sensor.

Moreover, the processing unit may be operatively coupled to an infusion device.

In a further aspect, the processing unit may include an insulin pump.

Moreover, in still another aspect, the processing unit may be is configured to determine the modification based on a pattern in the monitored analyte level, where the pattern may be determined based on the plurality of monitored analyte levels for a predetermined time period, and further, where the predetermined time period may include one of a 12 hour period, or 24 hour period.

The system in yet another embodiment may include a display unit operatively coupled to the processing unit for displaying the determined modification.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method, comprising:
collecting data associated with an analyte level of a patient using a sensor for a predetermined time period, the predetermined time period including a plurality of time of day segments;
retrieving a medication delivery profile executed during the predetermined time period including the plurality of time of day segments;
retrieving a predetermined parameter associated with one of the collected data associated with the analyte level, or the medication delivery profile; and
determining a modification to the medication delivery profile using a processing unit based at least in part on the collected data in conjunction with the retrieved predetermined parameter, or the medication delivery profile;
wherein determining the modification to the medication delivery profile includes determining a frequency of the analyte level deviating from a predetermined level during a first one of the plurality of time of day segments, and adjusting the medication delivery profile associated with the first one of the plurality of time of day segments when the frequency of the analyte level deviating from the predetermined level within the one of the plurality of time of day segments exceeds a predetermined frequency.

2. The method of claim 1 wherein the analyte is glucose.

3. The method of claim 1 wherein the predetermined parameter includes one or more of insulin sensitivity, a drug infusion rate, a drug infusion time period, a time period corresponding to a monitored analyte level, a time of day associated with the monitored analyte level, or a loop gain factor.

4. The method of claim 3 wherein the drug infusion rate is a basal profile.

5. The method of claim 1, wherein the medication delivery profile is adjusted when an occurrence of the analyte level deviating from the predetermined level within a second one of the plurality of time of day segments is detected.

6. The method of claim 5 wherein where the first and second ones of the plurality of time of day segments are sequential or adjacent in time.

7. The method of claim 1 further including outputting the determined medication delivery profile modification.

8. The method of claim 1 further including executing the modification to the medication delivery profile.

9. The method of claim 1 wherein the medication delivery profile includes an insulin infusion profile.

10. The method of claim 1 wherein the predetermined time period includes one of three days, five days or seven days.

11. The method of claim 1 wherein determining the modification to the medication delivery profile using the processing unit is performed retrospectively.

12. The method of claim 1 wherein determining the frequency of the analyte level deviating from the predetermined level is performed by the processing unit retrospectively.

13. An apparatus, comprising:
a data storage unit; and
a processing unit operatively coupled to the data storage unit for storing data or retrieving stored data, the processing unit configured to retrieve data associated with an analyte level of a patient for a predetermined time period including a plurality of time of day segments, to retrieve a medication delivery profile executed during the predetermined time period, to retrieve a predetermined parameter associated with one of the retrieved data associated with the analyte level, or the medication delivery profile, and to determine a modification to the medication delivery profile based at least in part on the retrieved data in conjunction with the retrieved predetermined parameter, or the medication delivery profile;
wherein the processing unit is configured to determine the modification to the medication delivery profile by determining a frequency of the analyte level deviating from a predetermined level during a first one of the plurality of time of day segments, and adjusting the medication delivery profile associated with the first one of the plurality of time of day segments when the frequency of the analyte level deviating from the predetermined level within the one of the plurality of time of day segments exceeds a predetermined frequency.

14. The apparatus of claim 13 wherein the processing unit includes an insulin pump.

15. The apparatus of claim 13 wherein the processing unit is configured to determine the modification based on a pattern in the retrieved data associated with the analyte level for the predetermined time period.

16. The apparatus of claim 15 wherein the pattern is determined based on an analysis of a plurality of monitored analyte levels received during the predetermined time period.

17. The apparatus of claim 13 wherein the predetermined time period includes one of three days, five days or seven days.

18. The apparatus of claim 13 further including a display unit operatively coupled to the processing unit for displaying the determined modification.

19. The apparatus of claim 13 wherein the analyte is glucose.

20. The apparatus of claim 16 wherein the analysis includes one or more of a rate of change analysis of the analyte level, a trend analysis of the analyte level, or an analysis of a medication delivery profile temporally associated with the analyte level.

21. The apparatus of claim 13 wherein the predetermined parameter includes one or more of insulin sensitivity, a drug infusion rate, a drug infusion time period, a time period corresponding to a monitored analyte level, a time of day associated with the monitored analyte level, or a loop gain factor.

22. The apparatus of claim 13 wherein the processing unit is operatively coupled to an infusion device.

23. A method, comprising:
receiving monitored glucose level information for a predetermined time period including a plurality of time of day segments from a sensor;
receiving an insulin basal profile administered during the predetermined time period;
retrieving a predetermined parameter associated with one of the received monitored glucose level information, or the insulin basal profile; and
determining using a processing unit an adjustment factor to the insulin basal profile based on the received monitored glucose level information, the retrieved predetermined parameter, or the insulin basal profile;
wherein determining the adjustment to the insulin basal profile includes determining a frequency of the analyte level deviating from a predetermined level during a first one of the plurality of time of day segments, and adjusting the insulin basal profile associated with the first one of the plurality of time of day segments when the frequency of the analyte level deviating from the predetermined level within the one of the plurality of time of day segments exceeds a predetermined frequency.

24. The method of claim 23 wherein the predetermined parameter includes one or more of insulin sensitivity, insulin infusion rate, insulin infusion time period, a time period corresponding to the monitored glucose level, a time of day associated with the monitored glucose level, or a loop gain factor.

25. The method of claim 23 including outputting the determined insulin basal profile adjustment factor.

26. The method of claim 23 including modifying the insulin basal profile based on the adjustment factor.

* * * * *